United States Patent [19]
Barbour et al.

[11] Patent Number: 6,077,515
[45] Date of Patent: *Jun. 20, 2000

[54] FLAGELLA-LESS BORRELIA

[75] Inventors: Alan G. Barbour, San Antonio, Tex.; Virgilio G. Bundoc, Newbury Park, Calif.; Adriadna Sadziene, San Antonio, Tex.

[73] Assignee: The University of Texas System, Board of Regents, Austin, Tex.

[*] Notice: This patent is subject to a terminal disclaimer.

[21] Appl. No.: 08/696,372

[22] Filed: Aug. 13, 1996

Related U.S. Application Data

[63] Continuation of application No. 08/124,290, Sep. 20, 1993, Pat. No. 5,585,102, which is a continuation of application No. 07/641,143, Jan. 11, 1991, Pat. No. 5,436,000.

[51] Int. Cl.[7] .......................... A61K 39/00; A61K 45/00; A01N 63/00; C12N 1/00
[52] U.S. Cl. ...................... 424/234.1; 424/184.1; 424/185.1; 424/282.1; 424/93.1; 424/93.4; 435/243; 435/245; 435/252.1
[58] Field of Search ............................ 424/234.1, 184.1, 424/185.1, 282.1, 93.1, 93.4; 435/243, 245, 252.1

[56] References Cited

U.S. PATENT DOCUMENTS 5,523,089  6/1996  Bergstrom et al. .................. 424/262.1

OTHER PUBLICATIONS

Dattwyler et al Annals of The New York Academy of Sciences vol. 539 pp. 93–102, 1988.
Szczepanski et al Microbiological Reviews 55:21–34, 1991.
Sadziene et al Journal of Clin Invest 88:82–92 1991.
Barbour et al Microbiological Reviews 50: 381–400, 1986.
Levine et al Research in Vet. Science 48:64–69 1990.
p. 66, ABST–B–242.
Burgess Annals of the New York Academy of Science 539:235–243, 1988.
Sadziene et al Abstracts of the 91st General Meeting of the American Society for Microbiology p. 66 ABST.–B–243.
Bundoc et al Abstracts of the 91st General Meeting of the American Society for Microbiology.

*Primary Examiner*—James C. Housel
*Assistant Examiner*—V. Ryan
*Attorney, Agent, or Firm*—Arnold White & Durkee

[57] ABSTRACT

This invention relates to flagella-less strains of Borrelia and to novel methods for use of the microorganisms as vaccines and in diagnostic assays. Although a preferred embodiment of the invention is directed to *Borrelia burgdorferi*, the present invention encompasses flagella-less strains of other microorganisms belonging to the genus Borrelia. Accordingly, with the aid of the disclosure, flagella-less mutants of other Borrelia species, e.g., *B. coriacei*, which causes epidemic bovine abortion, *B. anserina*, which causes avian spirochetosis, and *B. recurrentis* and other Borrelia species causative of relapsing fever, such as *Borrelia hermsii, Borrelia turicatae, Borrelia duttoni, Borrelia persica*, and *Borrelia hispanica*, can be prepared and used in accordance with the present invention and are within the scope of the invention. Therefore, a preferred embodiment comprises a composition of matter comprising a substantially pure preparation of a strain of a flagella-less microorganism belonging to the genus Borrelia.

5 Claims, 14 Drawing Sheets

FIG.1A

```
        -140                -120                -100
          •                   •                   •      •      •      •
CCTTGGATTTTACCGTTAAGCGCATGAAAGATCAAGAAAATACATTAAAGGCTTTTGATT

-80                 -60                 -40
          •                   •                   •      •     -35    •
TTAATCAAAGAAATAAATAATAATAATTATTTTTAATGCCATTGCTATCTGCGTTTCTTT

-20                 +1                   20
          •         -10       •        •           •           •
TTTTTAAATTTTGTGCTATTCTTTTAACAGGCAAAAGGATTTGCCAAAACCAAATAAT 40                  60                  80
          •                   •        1                       10
          •                   •        •           •           •
TAAATTTTATCATGGAGGAATGATATATGATTATCAATCATAATACATCAGCTATTAATG
             RBS             MetIleIleAsnHisAsnThrSerAlaIleAsnA 100                 120                 140
          •                   •       20                       30
          •                   •        •           •           •
CTTCAAGAAATAATGGCATTAACGCTGCTAATCTTAGTAAAACTCAAGAAAAGCTTTCTA
laSerArgAsnAsnGlyIleAsnAlaAlaAsnLeuSerLysThrGlnGluLysLeuSerS 160                 180                 200
          •                   •       40                       50
          •                   •        •           •           •
GTGGGTACAGAATTAATCGAGCTTCTGATGATGCTGCTGGCATGGGAGTTTCTGGTAAGA
erGlyTyrArgIleAsnArgAlaSerAspAspAlaAlaGlyMetGlyValSerGlyLysI 220                 240                 260
          •                   •       60                       70
          •                   •        •           •           •
TTAATGCTCAAATAAGAGGTTTGTCACAAGCTTCTAGAAATACTTCAAAGGCTATTAATT
leAsnAlaGlnIleArgGlyLeuSerGlnAlaSerArgAsnThrSerLysAlaIleAsnP 280                 300                 320
          •                   •       80                       90
          •                   •        •           •           •
TTATTCAGACAACAGAAGGGAATTTAAATGAAGTAGAAAAAGTCTTAGTAAGAATGAAGG
heIleGlnThrThrGluGlyAsnLeuAsnGluValGluLysValLeuValArgMetLysG 340                 360                 380
          •                   •      100                       110
          •                   •        •           •           •
AATTGGCAGTTCAATCAGGTAACGGCACATATTCAGATGCAGACAGAGGTTCTATACAAA
luLeuAlaValGlnSerGlyAsnGlyThrTyrSerAspAlaAspArgGlySerIleGlnI
```

FIG. 1B

```
              400             420             440
               .         120   .               .    130  .
TTGAAATAGAGCAACTTACAGACGAAATTAATAGAATTGCTGATCAAGCTCAATATAACC
leGluIleGluGlnLeuThrAspGluIleAsnArgIleAlaAspGlnAlaGlnTyrAsnG 460             480             500
               .         140   .               .    150  .
AAATGCACATGTTATCAAACAAATCTGCTTCTCAAAATGTAAGAACAGCTGAAGAGCTTG
lnMetHisMetLeuSerAsnLysSerAlaSerGlnAsnValArgThrAlaGluGluLeuG 520             540             560
               .         160   .               .    170  .
GAATGCAGCCTGCAAAAATTAACACACCAGCATCACTTTCAGGGTCTCAAGCGTCTTGGA
lyMetGlnProAlaLysIleAsnThrProAlaSerLeuSerGlySerGlnAlaSerTrpT 580             600             620
               .         180   .               .    190  .
CTTTAAGAGTTCATGTTGGAGCACCCCAAGATGAAGCTATTGCTGTAAATATTTATGCAG
hrLeuArgValHisValGlyAlaProGlnAspGluAlaIleAlaValAsnIleTyrAlaA 640             660             680
               .         200   .               .    210  .
CTAATGTTGCAAATCTTTTCTCTGGTGAGGGAGCTCAAACTGCTCAGGCTGCACCGGTTC
laAsnValAlaAsnLeuPheSerGlyGluGlyAlaGlnThrAlaGlnAlaAlaProValG 700             720             740
               .         220   .               .    230  .
AAGAGGGTGTTCAACAGGAAGGAGCTCAACAGCCAGCACCTGCTACAGCACCTTCTCAAG
lnGluGlyValGlnGlnGluGlyAlaGlnGlnProAlaProAlaThrAlaProSerGlnG 760             780             800
               .         240   .               .    250  .
GCGGAGTTAATTCTCCTGTTAATGTTACAACTACAGTTGATGCTAATACATCACTTGCTA
lyGlyValAsnSerProValAsnValThrThrThrValAspAlaAsnThrSerLeuAlaL 820             840             860
               .         260   .               .    270  .
AAATTGAAAATGCTATTAGAATGATAAGTGATCAAAGAGCAAATTTAGGTGCTTTCCAAA
ysIleGluAsnAlaIleArgMetIleSerAspGlnArgAlaAsnLeuGlyAlaPheGlnA 880             900             920
               .         280   .               .    290  .
ATGGACTTGAATCTATAAAGGATAGTACTGAGTATGCAATTGAAAATCTAAAAGCATCTT
snArgLeuGluSerIleLysAspSerThrGluTyrAlaIleGluAsnLeuLysAlaSerT
```

FIG. 1C

```
         940                 960                 980
                      300                         310
ATGCTCAAATAAAAGATGCTACAATGACAGATGAGGTTGTAGCAGCAACAACTAATAGTA
yrAlaGlnIleLysAspAlaThrMetThrAspGluValValAlaAlaThrThrAsnSerI 1000                1020                1040
                      320                         330
TTTTAACACAATCTGCAATGGCAATGATTGCGCAGGCTAATCAAGTTCCCCAATATGTTT
leLeuThrGlnSerAlaMetAlaMetIleAlaGlnAlaAsnGlnValProGlnTyrValL 1060                1080                1100
TGTCATTGCTTAGATAAAATTCTAGTTTAATTGGTATAAATTGTATTAACAAAAGATCCT
euSerLeuLeuArgEnd 1120                1140                1160
TTAAAGGATCTTTTGTTTTTTTATTTCAGATCGGCAAAAATTTAATAATTTTAGTATAAT 1180                1200                1220
TTATAATGATGTGTTATAAAGCCATAATGCAGGCTTATTGAGGAGTTTGCTTTGAGTAGG 1240                1260                1280
GTTGCTGTTAAAATTAAAGATTGTTATAAAGTATTTTCGTATTATGTTAACAAAAAGCAG 1300                1320                1340
ATAAGTCGAGCTATAAAAGACTATGAAGATGGCAAAGATAGAATGCAAATCTACAAAGAA

TCTTCTA
```

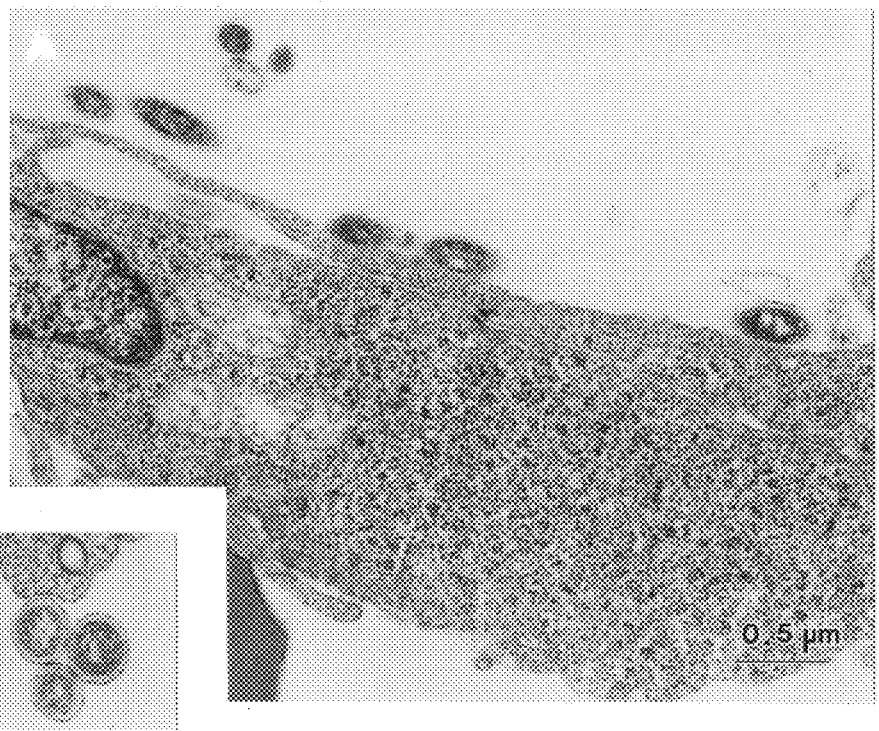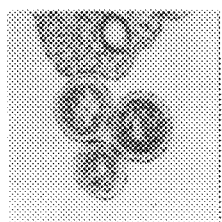

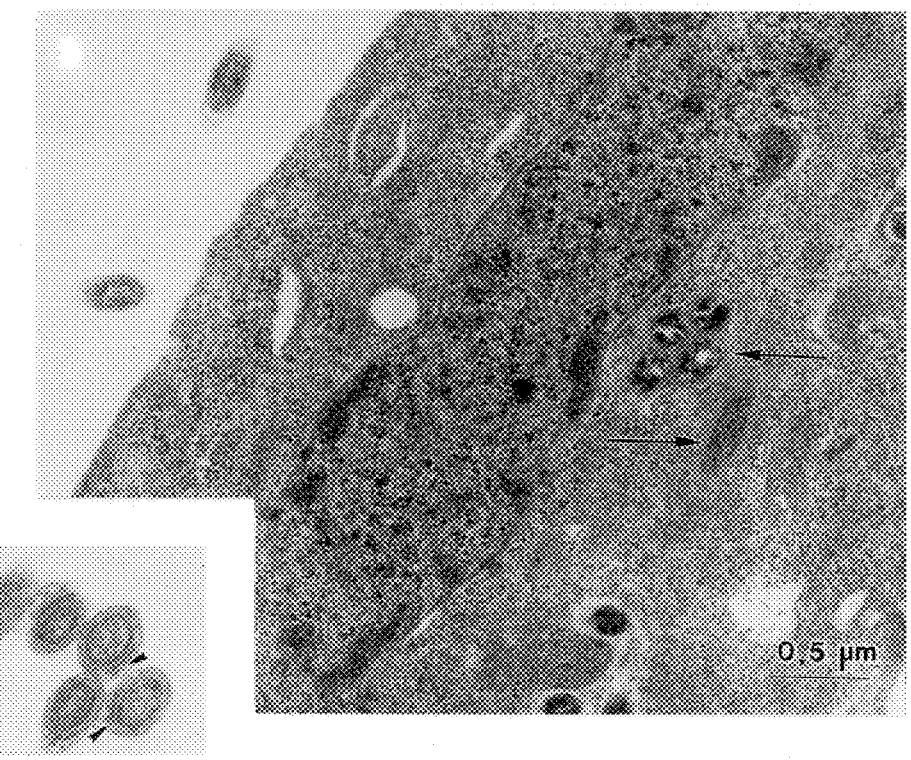
FIG.6B-I
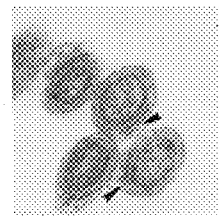
FIG.6B-II

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 1507 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Borrelia burgdorferi
      (B) STRAIN: HB19

(vii) IMMEDIATE SOURCE:
      (A) LIBRARY: pACA1

(ix) FEATURE:
      (A) NAME/KEY: CDS
      (B) LOCATION: 207..1217
      (D) OTHER INFORMATION: /product= "Flagellin"

(ix) FEATURE:
      (A) NAME/KEY: RBS
      (B) LOCATION: 194..198

(ix) FEATURE:
      (A) NAME/KEY: -10_signal
      (B) LOCATION: 146..151

(ix) FEATURE:
      (A) NAME/KEY: -35_signal
      (B) LOCATION: 122...125

(ix) SEQUENCE DESCRIPTION: SEQ ID NO:1:

```
CCTTGGATTT TACCGTTAAG CGCATGAAAG ATCAAGAAAA TACATTAAAG GCTTTTGATT        60

TTAATCAAAG AAATAAATAA TAATAATTAT TTTTAATGCC ATTGCTATCT GCGTTTCTTT       120

TTTTTAAATT TTTGTGCTAT TCTTTTTAAC AGGCAAAAGG ATTTGCCAAA ACCAAATAAT       180

TAAATTTTAT CATGGAGGAA TGATAT ATG ATT ATC AAT CAT AAT ACA TCA GCT       233
                            Met Ile Ile Asn His Asn Thr Ser Ala
                              1               5

ATT AAT GCT TCA AGA AAT AAT GGC ATT AAC GCT GCT AAT CTT AGT AAA       281
Ile Asn Ala Ser Arg Asn Asn Gly Ile Asn Ala Ala Asn Leu Ser Lys
 10              15                  20                  25

ACT CAA GAA AAG CTT TCT AGT GGG TAC AGA ATT AAT CGA GCT TCT GAT       329
Thr Gln Glu Lys Leu Ser Ser Gly Tyr Arg Ile Asn Arg Ala Ser Asp
                 30                  35                  40

GAT GCT GCT GGC ATG GGA GTT TCT GGT AAG ATT AAT GCT CAA ATA AGA       377
Asp Ala Ala Gly Met Gly Val Ser Gly Lys Ile Asn Ala Gln Ile Arg
             45                  50                  55

GGT TTG TCA CAA GCT TCT AGA AAT ACT TCA AAG GCT ATT AAT TTT ATT       425
Gly Leu Ser Gln Ala Ser Arg Asn Thr Ser Lys Ala Ile Asn Phe Ile
         60                  65                  70
```

-continued

| | | |
|---|---|---|
| CAG ACA ACA GAA GGG AAT TTA AAT GAA GTA GAA AAA GTC TTA GTA AGA<br>Gln Thr Thr Glu Gly Asn Leu Asn Glu Val Glu Lys Val Leu Val Arg<br>75                         80                           85 | 473 |
| ATG AAG GAA TTG GCA GTT CAA TCA GGT AAC GGC ACA TAT TCA GAT GCA<br>Met Lys Glu Leu Ala Val Gln Ser Gly Asn Gly Thr Tyr Ser Asp Ala<br>90                        95                       100                  105 | 521 |
| GAC AGA GGT TCT ATA CAA ATT GAA ATA GAG CAA CTT ACA GAC GAA ATT<br>Asp Arg Gly Ser Ile Gln Ile Glu Ile Glu Gln Leu Thr Asp Glu Ile<br>                    110                       115                       120 | 569 |
| AAT AGA ATT GCT GAT CAA GCT CAA TAT AAC CAA ATG CAC ATG TTA TCA<br>Asn Arg Ile Ala Asp Gln Ala Gln Tyr Asn Gln Met His Met Leu Ser<br>             125                       130                     135 | 617 |
| AAC AAA TCT GCT TCT CAA AAT GTA AGA ACA GCT GAA GAG CTT GGA ATG<br>Asn Lys Ser Ala Ser Gln Asn Val Arg Thr Ala Glu Glu Leu Gly Met<br>140                       145                       150 | 665 |
| CAG CCT GCA AAA ATT AAC ACA CCA GCA TCA CTT TCA GGG TCT CAA GCG<br>Gln Pro Ala Lys Ile Asn Thr Pro Ala Ser Leu Ser Gly Ser Gln Ala<br>155                       160                       165 | 713 |
| TCT TGG ACT TTA AGA GTT CAT GTT GGA GCA CCC CAA GAT GAA GCT ATT<br>Ser Trp Thr Leu Arg Val His Val Gly Ala Pro Gln Asp Glu Ala Ile<br>170                      175                     180                   185 | 761 |
| GCT GTA AAT ATT TAT GCA GCT AAT GTT GCA AAT CTT TTC TCT GGT GAG<br>Ala Val Asn Ile Tyr Ala Ala Asn Val Ala Asn Leu Phe Ser Gly Glu<br>             190                       195                     200 | 809 |
| GGA GCT CAA ACT GCT CAG GCT GCA CCG GTT CAA GAG GGT GTT CAA CAG<br>Gly Ala Gln Thr Ala Gln Ala Ala Pro Val Gln Glu Gly Val Gln Gln<br>             205                       210                     215 | 857 |
| GAA GGA GCT CAA CAG CCA GCA CCT GCT ACA GCA CCT TCT CAA GGC GGA<br>Glu Gly Ala Gln Gln Pro Ala Pro Ala Thr Ala Pro Ser Gln Gly Gly<br>220                       225                       230 | 905 |
| GTT AAT TCT CCT GTT AAT GTT ACA ACT ACA GTT GAT GCT AAT ACA TCA<br>Val Asn Ser Pro Val Asn Val Thr Thr Thr Val Asp Ala Asn Thr Ser<br>235                       240                       245 | 953 |
| CTT GCT AAA ATT GAA AAT GCT ATT AGA ATG ATA AGT GAT CAA AGA GCA<br>Leu Ala Lys Ile Glu Asn Ala Ile Arg Met Ile Ser Asp Gln Arg Ala<br>250                      255                     260                   265 | 1001 |
| AAT TTA GGT GCT TTC CAA AAT AGA CTT GAA TCT ATA AAG GAT AGT ACT<br>Asn Leu Gly Ala Phe Gln Asn Arg Leu Glu Ser Ile Lys Asp Ser Thr<br>             270                       275                     280 | 1049 |
| GAG TAT GCA ATT GAA AAT CTA AAA GCA TCT TAT GCT CAA ATA AAA GAT<br>Glu Tyr Ala Ile Glu Asn Leu Lys Ala Ser Tyr Ala Gln Ile Lys Asp<br>285                       290                       295 | 1097 |
| GCT ACA ATG ACA GAT GAG GTT GTA GCA GCA ACA ACT AAT AGT ATT TTA<br>Ala Thr Met Thr Asp Glu Val Val Ala Ala Thr Thr Asn Ser Ile Leu<br>             300                       305                     310 | 1145 |
| ACA CAA TCT GCA ATG GCA ATG ATT GCG CAG GCT AAT CAA GTT CCC CAA<br>Thr Gln Ser Ala Met Ala Met Ile Ala Gln Ala Asn Gln Val Pro Gln<br>315                       320                       325 | 1193 |
| TAT GTT TTG TCA TTG CTT AGA TAAAATTCTA GTTTAATTGG TATAAATTGT<br>Tyr Val Leu Ser Leu Leu Arg<br>330                     335 | 1244 |
| ATTAACAAAA GATCCTTTAA AGGATCTTTT GTTTTTTTAT TTCAGATCGG CAAAAATTTA | 1304 |
| ATAATTTTAG TATAATTTAT AATGATGTGT TATAAAGCCA TAATGCAGGC TTATTGAGGA | 1364 |
| GTTTGCTTTG AGTAGGGTTG CTGTTAAAAT TAAAGATTGT TATAAAGTAT TTTCGTATTA | 1424 |
| TGTTAACAAA AAGCAGATAA GTCGAGCTAT AAAAGACTAT GAAGATGGCA AGATAGAAT | 1484 |
| GCAAATCTAC AAAGAATCTT CTA | 1507 |

(2) INFORMATION FOR SEQ ID NO:2:

(i) SEQUENCE CHARACTERISTICS:
        (A) LENGTH: 336 amino acids
        (B) TYPE: amino acid
        (D) TOPOLOGY: linear (ii) MOLECULE TYPE: protein (ix) SEQUENCE DESCRIPTION: SEQ ID NO:2:

```
Met Ile Ile Asn His Asn Thr Ser Ala Ile Asn Ala Ser Arg Asn Asn
1               5                   10                  15

Gly Ile Asn Ala Ala Asn Leu Ser Lys Thr Gln Glu Lys Leu Ser Ser
            20                  25                  30

Gly Tyr Arg Ile Asn Arg Ala Ser Asp Asp Ala Ala Gly Met Gly Val
        35                  40                  45

Ser Gly Lys Ile Asn Ala Gln Ile Arg Gly Leu Ser Gln Ala Ser Arg
    50                  55                  60

Asn Thr Ser Lys Ala Ile Asn Phe Ile Gln Thr Thr Glu Gly Asn Leu
65                  70                  75                  80

Asn Glu Val Glu Lys Val Leu Val Arg Met Lys Glu Leu Ala Val Gln
                85                  90                  95

Ser Gly Asn Gly Thr Tyr Ser Asp Ala Asp Arg Gly Ser Ile Gln Ile
            100                 105                 110

Glu Ile Glu Gln Leu Thr Asp Glu Ile Asn Arg Ile Ala Asp Gln Ala
        115                 120                 125

Gln Tyr Asn Gln Met His Met Leu Ser Asn Lys Ser Ala Ser Gln Asn
    130                 135                 140

Val Arg Thr Ala Glu Glu Leu Gly Met Gln Pro Ala Lys Ile Asn Thr
145                 150                 155                 160

Pro Ala Ser Leu Ser Gly Ser Gln Ala Ser Trp Thr Leu Arg Val His
                165                 170                 175

Val Gly Ala Pro Gln Asp Glu Ala Ile Ala Val Asn Ile Tyr Ala Ala
            180                 185                 190

Asn Val Ala Asn Leu Phe Ser Gly Glu Gly Ala Gln Thr Ala Gln Ala
        195                 200                 205

Ala Pro Val Gln Glu Gly Val Gln Gln Glu Gly Ala Gln Gln Pro Ala
    210                 215                 220

Pro Ala Thr Ala Pro Ser Gln Gly Gly Val Asn Ser Pro Val Asn Val
225                 230                 235                 240

Thr Thr Thr Val Asp Ala Asn Thr Ser Leu Ala Lys Ile Glu Asn Ala
                245                 250                 255

Ile Arg Met Ile Ser Asp Gln Arg Ala Asn Leu Gly Ala Phe Gln Asn
            260                 265                 270

Arg Leu Glu Ser Ile Lys Asp Ser Thr Glu Tyr Ala Ile Glu Asn Leu
        275                 280                 285

Lys Ala Ser Tyr Ala Gln Ile Lys Asp Ala Thr Met Thr Asp Glu Val
    290                 295                 300

Val Ala Ala Thr Thr Asn Ser Ile Leu Thr Gln Ser Ala Met Ala Met
305                 310                 315                 320

Ile Ala Gln Ala Asn Gln Val Pro Gln Tyr Val Leu Ser Leu Leu Arg
                325                 330                 335
```

(2) INFORMATION FOR SEQ ID NO:3:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: DNA (genomic)

(ix) SEQUENCE DESCRIPTION: SEQ ID NO:3:

GCCAGCAGCA TCATCAGAAG                                                     20
```

FLAGELLA-LESS BORRELIA

This is a continuation of Ser. No. 08/124,290 filed Sep. 20, 1993 now issued as U.S. Pat. No. 5,585,102 issued Dec. 17, 1996, which is a continuation of U.S. Ser. No. 641,143 filed Jan. 11, 1991, issued as U.S. Pat. No. 5,436,000 on Jul. 25, 1995.

FUNDING

Development of the present invention was aided in part by finding from The National Institute of Health, grant no. AI24424. Accordingly, the U.S. Government has a paid-up license and the right in limited circumstances to require the patent owner to license others on reasonable terms as provided by the terms of Grant No. A124424.

FIELD OF THE INVENTION

This invention relates to flagella-less strains of Borrelia and in particular, *Borrelia burgdorferi*, and to novel methods for use of the microorganisms as vaccines and in diagnostic assays, particularly for Lyme disease.

BACKGROUND OF THE INVENTION

Lyme disease is a common tickborne infection of the northern hemisphere's temperature latitudes. The clinical features and epidemiology of Lyme disease have been well-characterized, and the etiologic agent, the spirochete *Borrelia burgdorferi*, has been isolated (reviewed by Steere, 1989). *Borrelia burgdorferi* enters the host's vascular system from the tick bite site and then is distributed to different organs and tissues, including the brain and joint synovium. In these different tissues the microorganism can persist for months to years. The properties of *Borrelia burgdorferi* that confer invasiveness in the human and other mammalian hosts have yet to be completely identified, although the flagellum has been implicated in pathogenicity.

Diagnosis of Lyme disease is complicated by the fact that the disease may mimic several other disorders, many of which are not infectious and, therefore, not ameliorated by antibiotics. A challenge for physicians is to identify cases of pauciarticular arthritis, radiculopathy, or extreme chronic fatigue as Lyme disease. If the clinical impression is confirmed by specific diagnostic assays, appropriate antimicrobial therapy may reverse long-standing pathologic changes. Unfortunately, physicians are often frustrated in this process by the inadequacies of currently available diagnostic procedures.

Recovery of *Borrelia burgdorferi* from patients is possible and should be considered diagnostic. However, the medium is expensive to keep stocked, cultures require up to 4 weeks of incubation for routine detection of spirochetes, and the frequency of isolating bacteria from the blood of acutely ill patients is less than 30%. Consequently, cultivation for *B. burgdorferi* is only done in a few institutions.

Direct detection of the etiologic agent in tissue or body fluids has also been attempted for diagnosis. For early Lyme disease, when the dermatologic hallmark erythema chronicum migrans is present, a Warthin-Starry or modified Dieterle silver stain reveals spirochetes in one-half or more of skin biopsies obtained from the outer portion of lesions (Duray, 1987; Berger, et al., 1983). The microorganisms are comparatively sparse, however, and can be confused with normal skin structures by inexperienced laboratory personnel. Immunohistologic examination of tissue with monoclonal and polyclonal antibodies has also been used successfully to show the presence of borreliae, but there is less experience with this technique than with the silver stains. (Park, et al., 1986).

Cases not meeting the strict clinical and epidemiologic criteria for diagnosis have also been identified as Lyme disease by using a serologic test, usually an enzyme-linked immunosorbent assay (ELISA) or in-direct immunofluorescence assay (IFA). Although many public and private laboratories now offer either ELISA or IFA, the procedures for these assays have not yet been standardized. The antigen preparations and the "cut-off" values for a positive test vary among laboratories. Significant interlaboratory variations in test results and in interpretations of the same set of sera have been reported (Hedberg, et al., 1987).

Many present immunoassays use whole spirochetes or a crude sonicate of the cells. However, those assays suffer from complications resulting from cross-reactions with other spirochetes, especially Treponema palladium and the relapsing fever Borrelia species (Magnarelli and Anderson, 1988), and borderline or low-level positive titers in some patients with other rheumatologic or neurologic disorders. Because of increasing professional and lay awareness of Lyme disease, serologic testing is often requested to "rule out" the diagnosis. In this situation, the ratio of persons with false-positive reactions compared with those who have actual *Borrelia burgdorferi* infections will predictably rise. Thus, "seropositive" patients with disorders other than Lyme disease may be subjected to long and possibly hazardous courses of oral or parenteral antibiotics. A more specific diagnostic assay for *B. burgdorferi* is needed.

Although several investigators have suggested use of an immunoassay using a purified flagella protein antigen, there are problems with this approach. For one thing, it has recently been shown that a monoclonal antibody directed against the major flagella protein of *Borrelia burgdorferi* also recognizes human tissue, including myelin and Schwann cells from the peripheral nervous system (Sigal, et al., 1988; Aberer, et al., 1989). Autoantibodies against neural antigens have been observed in the serum of patients with Lyme disease. These findings suggest that autoreactive antibodies may complicate interpretation of immunoassays that use purified flagellar antigen or whole cell sonicates containing flagella antigen. Another problem with the use of preparations containing the flagellum by itself or in combination with other components is that there may be false positive reactions as a consequence of antigenic similarities between the flagella of borreliae and the flagella of other bacteria.

The discovery that flagellar antigens may induce formation of antibodies reactive with human neural tissue provides an additional problem with respect to development of a vaccine against Lyme Disease. International Patent Application No. WO 90/04411, published May 3, 1990 describes a method for preparing fractions of *Borrelia burgdorferi* in which the flagellar components are at least partially depleted. However, that method is somewhat time consuming and labor intensive. Inactivated whole cell *Borrelia burgdorferi* vaccines, such as those described in U.S. Pat. No. 4,721,617 and by Johnson, et al., 1986, comprise a relatively high proportion of the flagellar antigen and may thus induce an undesirable auto immune response. In addition, because flagellated Borrelia is virulent, the cells must be killed prior to administration, thus reducing immunogenicity. Because the flagellum is an important virulence factor of the organism, development of a flagellar-less strain could provide an ideal approach for development of an attenuated vaccine.

Flagella-less strains of other Borrelia pathogens such as *Borrelia coriacei*, which is associated with epidemic bovine abortion, *Borrelia anserina*, which causes avian spirochetosis, *Borrelia recurrentis, Borrelia hermsii, Borrelia turicatae, Borrelia duttoni, Borrelia persica*, and *Borrelia hispanica*, which cause relapsing fever, and any of a number of other Borrelia pathogens would possess similar advantages.

SUMMARY OF THE INVENTION

Many of the problems set forth above have now been overcome by the present invention, which provides a novel flagella-less strain of *Borrelia burgdorferi* suitable for use as a vaccine and/or use in immunoassay. Because the *Borrelia burgdorferi* strain of the invention does not possess the flagella antigen associated with autoantibody formation, it can advantageously be used to immunize individuals against Lyme disease without the risk of vaccine-induced autoantibody formation associated with whole cell vaccines described previously or with subunit vaccines which may be contaminated with the flagella. In addition, because the flagellum may play an important role in determining virulence of the organism, the vaccine of the present invention is likely to be safer than whole cell *Borrelia burgdorferi* preparations described in the past, and thus may be administered as a live vaccine. Moreover, the organism may be used in immunoassay, alone or in conjunction with a flagellated strain, without the complications of the potential contribution of auto-antibodies or antibodies cross-reactive with borrelial flagella resulting from immunogenic exposure to non-borrelial flagella.

Although a preferred embodiment of the invention is directed to *Borrelia burgdorferi*, the present invention encompasses any flagella-less strain of a microorganism belonging to the genus Borrelia. Accordingly, with the aid of the present disclosure, flagella-less mutants of other Borrelia species, e.g., *B. coriacei*, which causes epidemic bovine abortion, *B. anserina*, which causes avian spirochetosis, and *B. recurrentis* and other Borrelia species causative of relapsing fever, such as *Borrelia hermsii, Borrelia turicatae, Borrelia duttoni, Borrelia persica*, and *Borrelia hispanica*, can be prepared and used in accordance with the present invention and are within the scope of the invention. Thus, the invention includes a culture of the flagella-less borreliae, a composition of matter comprising a substantially pure preparation of a flagella-less strain of such a microorganism, and a composition of matter comprising a purified preparation of antigens derived from a culture of a flagella-less strain of such a microorganism.

Also included is an immunoassay procedure for detection of Borreliosis, i.e., infection with borreliae, comprising obtaining a biological sample, such as a sample of a bodily fluid, such as blood, serum, plasma, urine, or synovial or cerebrospinal fluid, from an individual to be tested, contacting the sample with an antigenic preparation derived from a culture of a selected flagella-less strain of borreliae under conditions suitable to allow binding between the antigens in the preparation and borreliae-reactive antibodies in the sample and detecting the binding.

So called "agglutination" assays may be used in accordance with the present invention. In one example, a "latex agglutination" assay, the antigenic preparation is adsorbed or chemically coupled to a particle, such as a latex bead, and particles bearing the antigen are agglutinated under conditions which allow crosslinking of antigen molecules on discrete particles by antibody-antigen complex formation. Alternatively, the antigenic preparations can be used in a so called "microagglutination" or "flocculation" assay, where clumps of antigen-antibody complexes are observed directly.

In another embodiment, the immunoassay may comprise what is known to those of skill in the art as a competitive immunoassay; in such an assay binding is detected by adding a preparation of labeled antibodies reactive with a selected flagella-less Borrelia strain to the contacted sample and measuring binding of the labeled antibody to the antigenic preparation. Because antibodies in the sample will compete with the labeled antibodies for antigenic epitopes in the antigen preparation, binding of the labeled antibody will be inversely proportional to the concentration of antibody in the sample.

Alternatively, the immunoassay procedure may be an immunoassay wherein the binding is detecting by adding to the contacted sample a preparation of labeled antibodies that are capable of binding to the antibodies in the sample (e.g., anti-immunoglobulin antibodies) under conditions suitable to allow binding between the labeled antibodies and the antibodies in the samples and measuring the amount of the labeled antibody bound to the antigen-bound antibodies.

Any of a number of different detectable labels known to those of skill in the art for use in immunoassay may be used in these procedures, including, for example, radioactive labels, fluorescent labels, enzymatic labels (such as peroxidase) capable of cleaving a selected substrate to produce a colored product, or a first member of a selected binding pair such as biotin and avidin, or Staph protein A and IgG. When binding pairs are used, the first member will usually have a binding affinity of at least about $10^6$ liters/mole for the second member of the binding pair, which second member also generally includes a detectable label of the type described above. The measuring step may be performed by contacting the first member, such as the biotin moiety on a biotinylated anti-immunoglobulin antibody, with the second member (such as labeled avidin) of the pair and detecting binding between the members.

The invention also includes procedures for detecting antibodies capable of binding to non-flagellar antigens of microorganisms of a selected Borrelia species, preferably *Borrelia burgdorferi*. Those procedure comprises obtaining a sample to be tested for the antibodies, contacting the sample with an antigenic preparation, derived from a culture of a flagella-less strain of the selected Borrelia species, under conditions suitable to allow binding between the antigens in the preparation and the antibodies, and detecting the binding. In a preferred embodiment, the immunoassay will comprise a solid-phase immunoassay procedure for detecting antibodies capable of binding to non-flagellar antigens of a selected Borrelia species. That assay comprises immobilizing an antigenic preparation derived from a culture of a flagella-less strain of the Borrelia species on a solid matrix, contacting the immobilized preparation with a sample to be tested for the presence of the antibodies under conditions suitable to allow binding between the antigens in the preparation and the antibodies, separating antibodies bound to the immobilized antigens from the remainder of the sample, and detecting the antigen-bound antibodies. Also included is an additional solid-phase immunoassay for detecting antibodies capable of binding to non-flagellar antigens of a selected Borrelia species comprising obtaining a sample from an individual to be tested, immobilizing antibodies present in the sample on a solid matrix, separating the immobilized antibodies from the sample, contacting the immobilized antibody with an antigenic preparation derived from a flagella-less strain of the selected Borrelia species under conditions suitable to allow binding between the antigens in the preparation and the antibodies, and detecting the antigen-bound antibodies. With this method, the antibodies are detected by contacting the antigen-bound antibody with a detectably labeled antibody capable of specifically binding to the antigen-bound antibody under conditions suitable to allow the binding to occur.

Although the assays may be performed with samples from a number of tissues and bodily fluids, in preferred embodiments, the sample is either serum or plasma, or cerebrospinal or synovial fluid, or urine.

The invention also includes a number of kits for immunoassay. Such kits may comprise, for example, a carrier compartmentalized to contain one or more containers, and a first container containing an antigenic preparation derived from a flagella-less strain of a selected Borrelia species. In one embodiment, the antigenic preparation may be provided immobilized on a solid phase, such as a microtiter well or latex bead. The kit may further comprise a second container comprising a preparation of antibodies reactive with the antigens in the antigenic preparation, and/or a third container containing a detection reagent.

The invention includes vaccines for Borreliosis and vaccination procedures. Vaccines according to the present invention may comprise, for example, an antigenic component derived from a culture of a flagella-less Borrelia strain and a pharmaceutically acceptable carrier. As with other aspects of the invention, the vaccine can comprise any of a number of selected Borrelia species, including but not limited to *B. coriacei*, for prevention of epidemic bovine abortion; *B. recurrentis, B. hermsii, B. turicatae, B. duttoni, B. persica*, and *B. hispanica*, for prevention of relapsing fever; and *B. anserina* for prevention of avian spirochetosis. Preferably, however, the vaccine will be preventative of Lyme disease in which case it will include an antigenic component derived from a flagella-less strain of *B. burgdorferi*.

The invention also includes a method for inducing an immune response of a mammal or bird to a microorganism belonging to the genus Borrelia comprising administering an immunogenic dose of the vaccine to the mammal or bird. As those of skill in the art will appreciate, a number of mammals are infected with or are carriers of Borrelia pathogens and thus the invention is not limited by a particular mammal to be injected with the vaccine derived from a particular Borrelia species. However, preferred combinations are those most likely to elicit control or prevention of a commercially significant pathogen. Consequently, vaccines comprising antigens from *B. burgdorferi* will usually be administered to the primary victims or carriers of Lyme disease such as humans, dogs, horses, equids, cattle (victims), deer and rodents, (particularly mice) (carriers). Vaccines comprising antigens derived from *B. coriacei* are usually administered to cattle and those comprising *B. anserina*, to birds, particularly poultry. Vaccines comprising *B. recurrentis* and other Borrelia pathogens causing relapsing fever are usually administered to humans.

In addition to the reduced potential for elicitation of undesirable autoimmune responses and the ability to be administered as live attenuated vaccines, the novel vaccines possess the additional advantage of facilitating diagnosis of Borreliosis in individuals, mammals, and birds who have been administered the vaccine. As those of skill in the art will recognize, few if any vaccines are one hundred percent efficacious and vaccine failures do occur. Furthermore, when the disease vaccinated against is a disease which, like Lyme disease, elicits symptoms that can be attributed to a number of other pathologic conditions, specific immunodiagnostic assays may be complicated by antibodies elicited against the vaccine. In contrast, when the flagella-less microorganisms of the present invention are used for immunization, one can simply assay an individual exhibiting symptoms characteristic of a selected borrelial pathogenesis, such as Lyme disease, for antibodies to the flagellar-antigen. In such individuals, the absence of such antibodies will usually weigh against a diagnosis of Borreliosis, and their presence will be suggestive of a vaccine failure.

These and other aspects of the invention will become more apparent from a description of particular embodiments when read in conjunction with the drawings.

DESCRIPTION OF THE DRAWINGS

FIG. 1: The oligonucleotide 5'-GCCAGCAGCATCATCAGAAG-3' SEQ. ID. NO. 3, which represented a conserved sequence of fla genes of two other strains of *B. burgdorferi* (Gassmann, et al., 1989), was synthesized and used to identify a flagellin gene-bearing clone in a library of genomic DNA of strain HB19 of *B. burgdorferi* in λFIX II. A 5.0 kb Bgl II fragment containing the complete fla gene of strain HB19 was subcloned into the plasmid vector pBR322 to yield recombinant plasmid pACA1. The nucleotide sequence of both strands of the flagellin gene and its 5' and 3' flanking sequences in pACA1 were determined by primer-directed sequencing of double-stranded pACA1 plasmid DNA. The start of transcription of flagellin gene was identified by primer extension analysis of total RNA isolated from strain HB19 *B. burgdorferi*. The analysis revealed the following: (i) the coding region for the flagellin gene of strain HB19 from positions 58–1065; (ii) the transcriptional start site, the C at position +1, 57 bp distant from the start codon; (iii) the likely ribosomal binding site (RBS) as GGAGG at position 45 to 49; and (iv) the likely "−10" (GCTATT) and "−35" (CGTT) promoter boxes. The numbers in the top column refer to nucleotides, those in the bottom column to amino acids. See SEQ. ID. No. 1.

FIG. 6: Thin-section electron photomicrographs of penetration of HUVE cells by M and R isolates of *Borrelia burgdorferi* strain HB19.

a) transverse section showing the M spirochetes attached to the surface of, but not within, a HUVE cell; bar equals 1.0 μm. (Inset) Cross section of M spirochetes demonstrating lack of axial flagella (arrows).

b) Micrograph showing R spirochetes (arrows) within a HUVE cell. Bar equals 1.0 μm. (Inset) Cross section of R spirochetes, which possess axial flagella (arrows).

Figure 7:
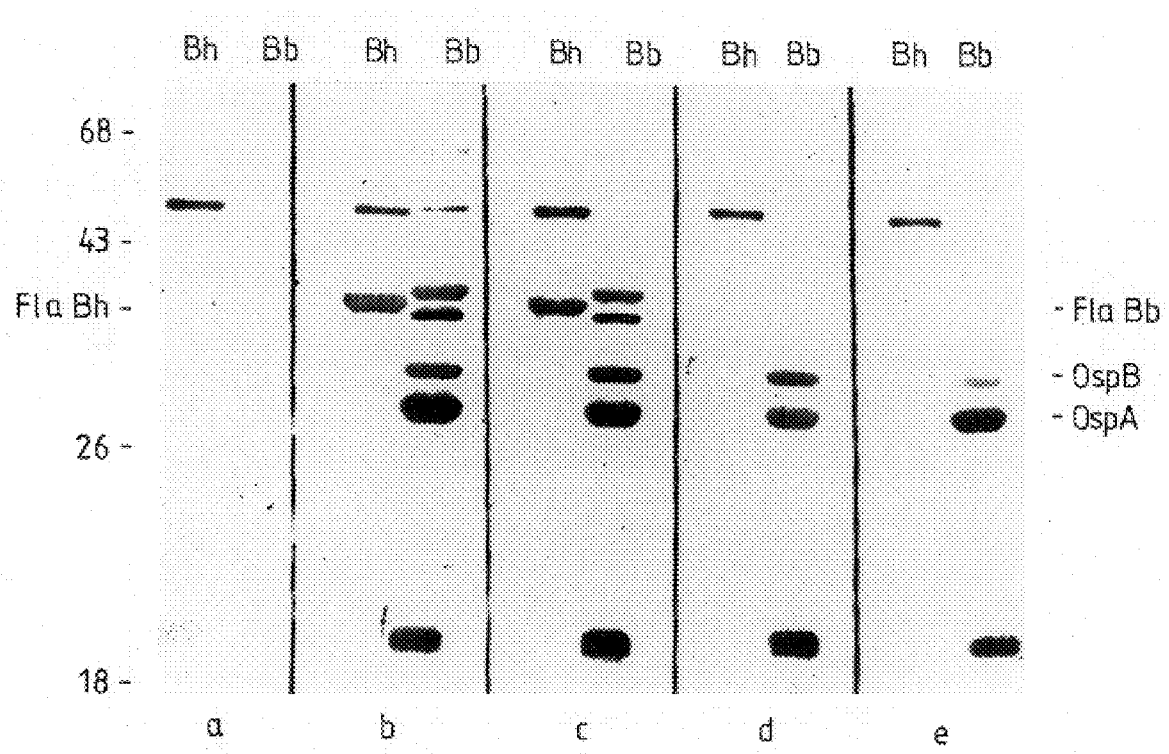

FIG. 7: Western blot analysis of serum from Fisher rats to components of *B. hermsii* (*Bh*) and *B. burgdorferi* (*Bb*). Panels a–e represent the following:

a) normal rat;

b) and c) rats immunized with whole W cells;

d) and e) rats immunized with whole M cells.

To the left are indicated the relative migrations of the molecular weight standards (in kDa). The locations of flagellins of *B. hermsii* (Fla *Bh*) and *B. burgdorferi* (Fla *Bb*) and the OspA and OspB proteins in the blot are shown.

DESCRIPTION OF A PREFERRED EMBODIMENT

The flagella-less Borrelia strains of the present invention may be advantageously used in immunoassay procedures or as vaccine components.

Suitable immunoassays for use with the flagella-less Borrelia strains of the invention include assays employing a number of principles well known to those of skill in the art, including those described by Nisonoff, *Introduction to Molecular Immunology*, 2nd Ed., Sinaues Associates, Inc., Sunderland, Mass. (1984) and in U.S. Pat. No. 4,376,110, both incorporated herein by reference.

Generally, for detection of antibody in biologic samples, such as blood, plasma, serum, cerebrospinal fluid, synovial fluid, urine and the like, the flagella-less borreliae as antigen, or an antigenic composition prepared therefrom, is preferably adsorbed, or otherwise attached, to an appropriate adsorption matrix (for example, the inside surface of a microtiter dish or well) and a sample of a suspected antibody-containing composition is contacted therewith to cause formation of an immunocomplex between antigens in the composition and any antibodies in the sample that bind to those antigens. The matrix is then washed to remove non-specifically bound material and the immunocomplexes are detected, typically through the use of an appropriate labeled ligand.

Antigen compositions comprising flagella-less borreliae may also be incorporated into diagnostic kits useful in performing assays of the type described above. A number of kits might be utilized in the practice of the present invention, for example, a kit comprising a carrier compartmentalized to contain at least one, at least two, or at least three or more containers.

A first container may include a composition comprising an antigen preparation of the flagella-less borreliae, which may include whole cell preparations or lysates of flagella-less microorganisms or preparations including partially or substantially purified antigenic components derived therefrom, and in particular, cell surface protein antigens. The kits may also include antibody compositions having specificity for one or more Borrelia antigens. Both antibody and antigen preparations should preferably be provided in a suitable titrated form, with antigen concentrations and/or antibody titers given for easy reference in quantitative applications, although the antigenic preparation may also be provided immobilized on a solid matrix.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for the antigen or first antibody. Thus, the reaction is detected or quantified by means of detecting or quantifying the label. Immunodetection reagents and processes suitable for application in connection with the novel compositions of the present invention are generally well known in the art.

The flagella-less borreliae of the invention may also be effectively used as vaccines to prevent Borreliosis, and Lyme disease in particular. In general, immunogenic compositions suitable for administration as vaccines could be formulated to include the flagella-less borreliae, whole cell lysates thereof, or purified antigenic preparations derived from the flagella-less borreliae. Typically, such vaccines are prepared as injectables, either as liquid solutions or suspensions, although solid forms suitable for solution in, or suspension in, liquid prior to injection may also be prepared. The preparations may also be emulsified. The reactive immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine could contain minor amounts of auxiliary substances such as wetting or emulsifying agents, pH buffering agents, or adjuvants which enhance the effectiveness of the vaccine.

The antigens can be formulated into the vaccine as neutral or salt forms and administered in a manner compatible with the dosage formulation, and in such amount as will be therapeutically effective and immunogenic. The vaccines may be conventionally administered parenterally, by injection, for example, either subcutaneously or intramuscularly. Where a live vaccine is used, preferred modes of administration are subcutaneous and intradermal injection. Additional formulations which are suitable for other modes of administration may include oral or intranasal formulations. The quantity to be administered will depend on the subject to be treated, capacity of the immune system to synthesize antibodies, and the degree of protection desired. Precise amounts of active ingredient required to be administered will depend on the judgment of the practitioner and may be peculiar to each individual. However, suitable dosage ranges may be on the order of 0.01 ug to 10 mg, and more preferably 1 to 100 ug active ingredient per kilogram of body weight. Suitable regimes for initial administration and booster shots will also be variable, but may be typified by an initial administration followed by subsequent inoculations or other administrations.

In many instances, it may be desirable to have multiple administrations of the vaccine, at from two to twelve week intervals, more usually from three to five week intervals. Periodic boosters at intervals of 1–5 years, usually three years, will be desirable to maintain protective levels of the antibodies. The course of the immunization may be followed by assays for antibodies for the antigens as described above.

These and other embodiments of the invention may be more readily understood from examination of the examples set forth below. However, the subject matter set forth in the examples is not intended to limit the scope of the invention unless specifically specified in the claims.

EXAMPLE I

The following example provides methods for producing a culture of flagella-less *Borrelia burgdorferi* for use in accordance with this invention with the aid of the present disclosure. The methods may also be used to generate flagella-less borreliae of other species including but not limited to *Borrelia anserina, Borrelia recurrentis, Borrelia hermsii, Borrelia turicatae, Borrelia duttoni, Borrelia persica*, and *Borrelia hispanica*, and *Borrelia coriacei*.

According to the invention and with the aid of the present disclosure, one may produce a culture of flagella-less *Borrelia burgdorferi* according to the following general procedures: First, one clones a population of *B. burgdorferi* by limiting dilution in BSK medium without Yeastolate and selects any non-motile clones having a non-helical morphology. The clones are then subcultured in Yeastolate-free BSK. Alternatively one may clone a population of *B. burgdorferi* by single-colony plating on BSK medium with agarose and incubation in low-oxygen and high-carbon dioxide atmosphere and selection of compact rounded colonies with distinct edges. Those clones are then subcultured in BSK without Yeastolate and non-motile variants are selected as described above.

In some circumstances, it may be desirable to mutagenize the starting population of *B. burgdorferi*, for example, with chemicals, such as nitrosoguanidine, or irradiation, such as gamma-rays, in order to increase the frequency of mutation. The mutagenized *B. burgdorferi* are then selected by cloning by limiting dilution or by colony formation as described above. Another procedure which could be used comprises transposon mutagenesis of the flagellin gene followed by selection in antibiotic-containing BSK medium without Yeastolate (BSK I), and further selection for flagella-less mutants as described above. With the aid of the present disclosure, one may also devise methods for preparing flagella-less strains by recombinant DNA technology, for example, in vitro mutagenesis of the cloned flagellin gene and transformation of the mutant gene back into the borrelia. The sequence of the cloned flagellin gene and the 3' and 5' flanking sequences is shown in FIG. 1. The cloned flagellin gene could be accompanied by an antibiotic selection marker to aid selection of transformants in broth medium or on solid medium. Antibiotic-resistant transformants would be examined as to flagella phenotype. With any of these procedures, the mutations may be in the gene itself or in the regulatory regions, such as the promoter or terminator, for the flagellin gene. More specifically, such mutations can include deletion of the entire coding region of the gene or portions thereof, deletion or mutagenesis of the ribosomal binding sequence (RBS), deletion or mutagenesis of the −10 and −35 promoter boxes, or insertion or deletion of DNA transcribed sequence of the gene such that a functional flagellar protein is not produced.

EXAMPLE II

This example describes mutant isolation and characterization of a mutant designed below as (M), now deposited with the ATCC pursuant to the Budapest Treaty and having accession #55131.

Strains and culture conditions

Strain HB19, the first human blood isolate of *B. burgdorferi* (Steere et al., 1983; Barbour et al., 1984), was cloned four times by limiting dilution or colony plating (Bundoc and Barbour, 1989). The cells were grown in BSK I (Barbour-Stoener-Kelly) medium at 34° C. in tightly-capped polystyrene tubes (Barbour, et al. 1983b); in some experiments, BSK II medium (Barbour 1984) which is BSK I medium supplemented with Yeastolate, was used. Cells were harvested by centrifugation (10,000×g for 20 min) and washed 3 times with phosphate-buffered saline, pH 7.2 (PBS), with 5 mM Mg (PBS/Mg). For routine passage 0.4% vol/vol of a culture at a bacterial concentration of $10^8$ cells per milliliter was inoculated into a fresh tube of medium. Cells were counted using a Petroff-Hauser chamber adapted for use with phase contrast microscopy. Cells were cloned by limiting dilution in broth medium by making a 10-fold dilutions into 10 tubes at each dilution (Bundoc and Barbour, 1989). These cultures were blindly passed to fresh medium after 3 weeks incubation and examined by phase contrast microscopy weekly. Borreliae were grown as colonies on BSK I medium with 1.5% agarose in candle jars at 34° C. (Bundoc and Barbour, 1989). Colonies on the plates were picked as plugs with sterile pasteur pipettes and inoculated into broth BSK I medium supplemented with rifampin (50 ug/ml) and phosphomycin (100 ug/ml).

The discovery of the mutant 55131 was made during successive cloning of *Borrelia burgdorferi* strain HB19. The population of HB19 used for the fifth cloning was designated "W" for wild type; approximately 300 generations had occurred since the fourth cloning. Out of the 3 of 10 tubes at the highest dilution that had borrelial growth (at an average of one cell per tube, 33% of the tubes will exhibit growth), one contained cells that differed substantially in appearance from W-type cells in the other two tubes. When examined by phase microscopy, the variant cells were non-motile instead of motile and straight instead of helical. Variant cells also differed form the W-type cells in their tendency to aggregate into bundles of thin straight cells and to produce less color change in the medium's phenol red indicator at equivalent cell densities during logarithmic phase growth.

A sample of the variant cell population was plated on BSK agar for a second round of cloning. Four well-isolated colonies were picked and grown in broth medium. These other clonal populations had the same non-motile straight phenotype when examined by phase contrast microscopy. One of the second group of clones was arbitrarily selected for use in subsequent experiments and was designated "M" for mutant.

When the M cells were passed in BSK I medium, at least 99.9% of the cells in each tube's population remained non-motile and straight after 10 to 15 passages, or 80 to 120 generations. However, when the M mutant was passed in complete BSK II, i.e., which contains yeastolate, helical cells constituted at least 0.1% of the cell population in the culture tubes after 3 to 6 passages, or 24 to 48 generations.

When the mixed cultures were subsequently continuously passed in BSK II medium, the motile helical cells predominated. Thereafter, the population retained the wild-type phenotype even when reactivated in BSK I medium. This motile population which was designated "R", was subsequently cloned by limiting dilution and used in subsequent experiments.

Electron microscopy

For negative-staining studies, harvested borreliae were resuspended in one-tenth volume of PBS. The cells were applied to carbon-coated 300 mesh grids and stained for 30 sec. with 2% (w/v) ammonium molybdate, pH 7.2, in distilled water. Excess fluid was removed with absorbent paper. The grids were then air-dried and immediately examined in a JEOL EM 1200 transmission electron microscope.

When negatively-stained preparations of W, M, and R isolates were examined by electron microscopy as described above, it was observed that the motile and helical W and R isolates had full-length axial flagella (AF) running between the outer sheath (OS) and protoplasmic cylinder (PC) (FIG. 2). In contrast, the non-motile, non-helical M isolate has pores (AFP) for the flagella but no flagella. Hooks could also be seen in the pores of the M cells. These studies confirmed that the M cells were lacking in flagella.

Polyacrylamide gel electrophoresis and Western blot analysis

Figures 2A, 2B:
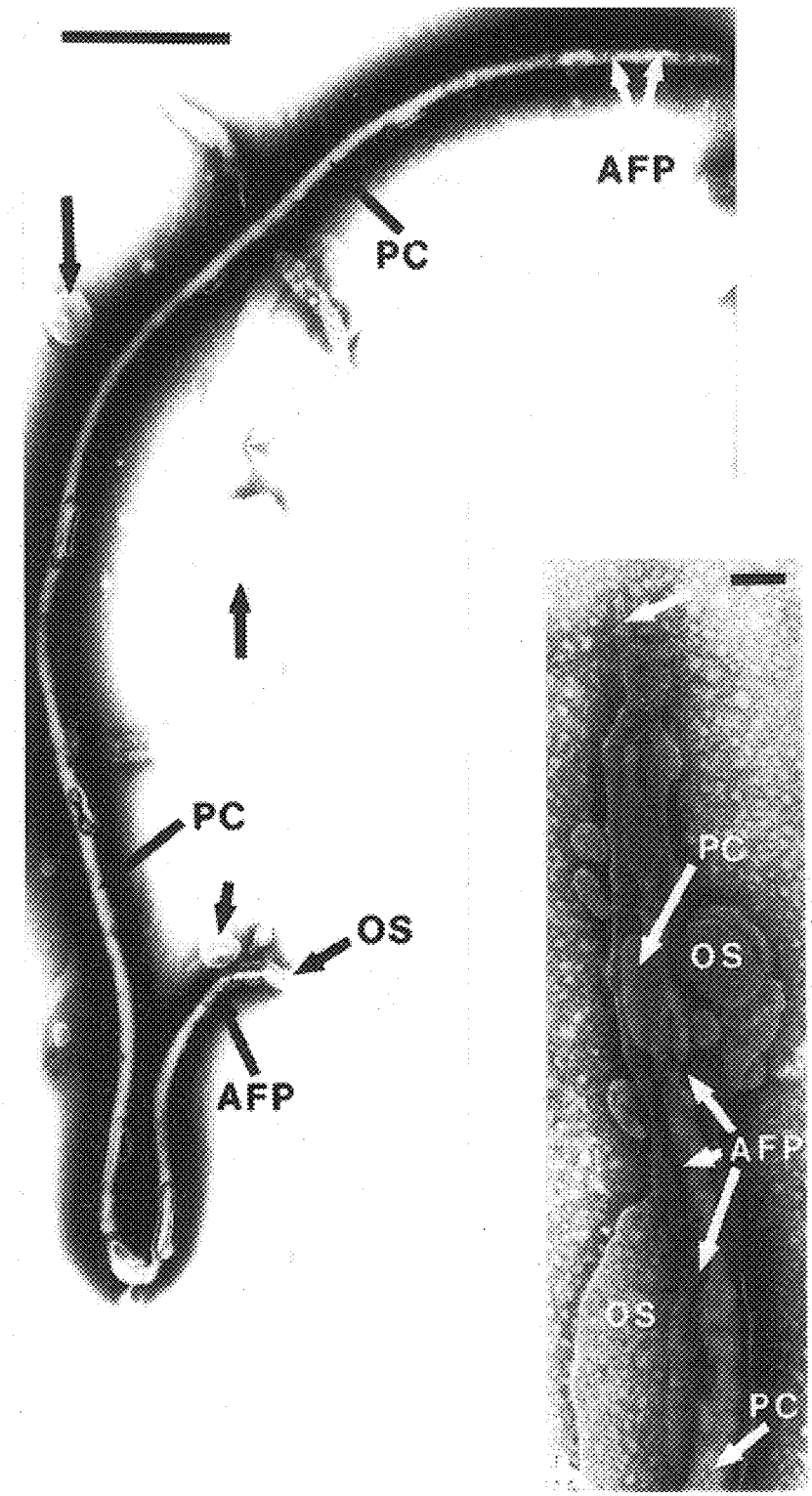
FIG. 2: Electron photomicrographs of negatively-stained W, M, and R cells of *Borrelia burgdorferi* strain HB19. W cells (plates d and f) possess numerous axial flagella (AF) which overlay the helical protoplasmic cylinder (PC). The loose-fitting outer sheath (OS) encloses the cell. Axial flagella pores (AFP) are also apparent. The non-helical M cells (a,b) possess a loosely fitting outer sheath and axial flagella pores with hook protein. However, M cells do not have axial flagella. R cells (e) have axial flagella like W cells. Bar equals 1.0 μm (a,c,d,f), 0.5 μm (e), or 0.1 μm (b).
Figure 2C:
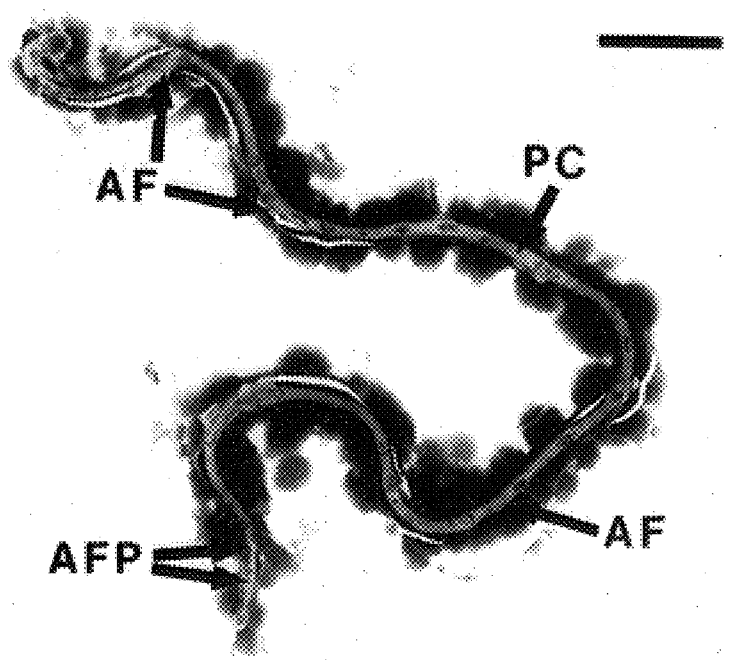
Figure 2D:
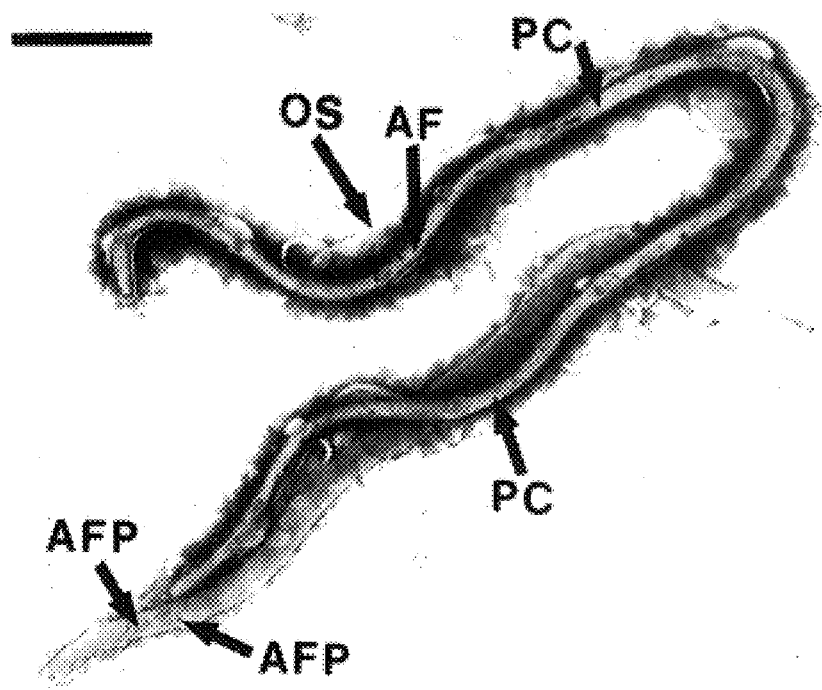
Figure 2E:
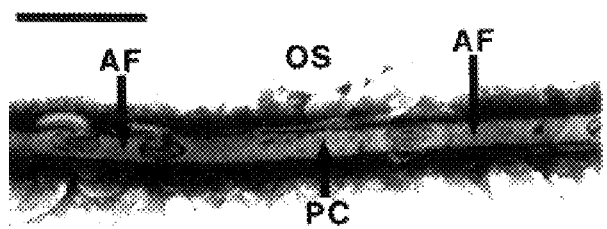
Figure 2F:
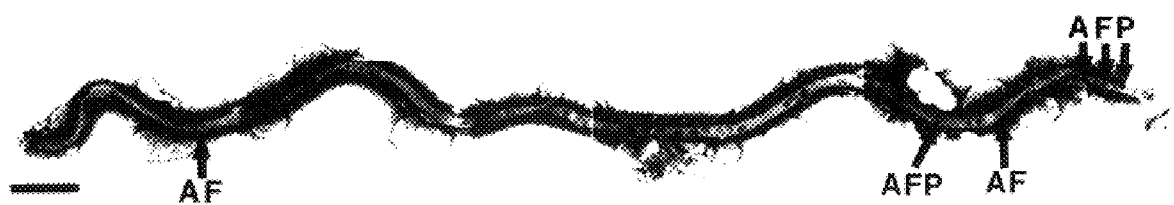
Figure 3:
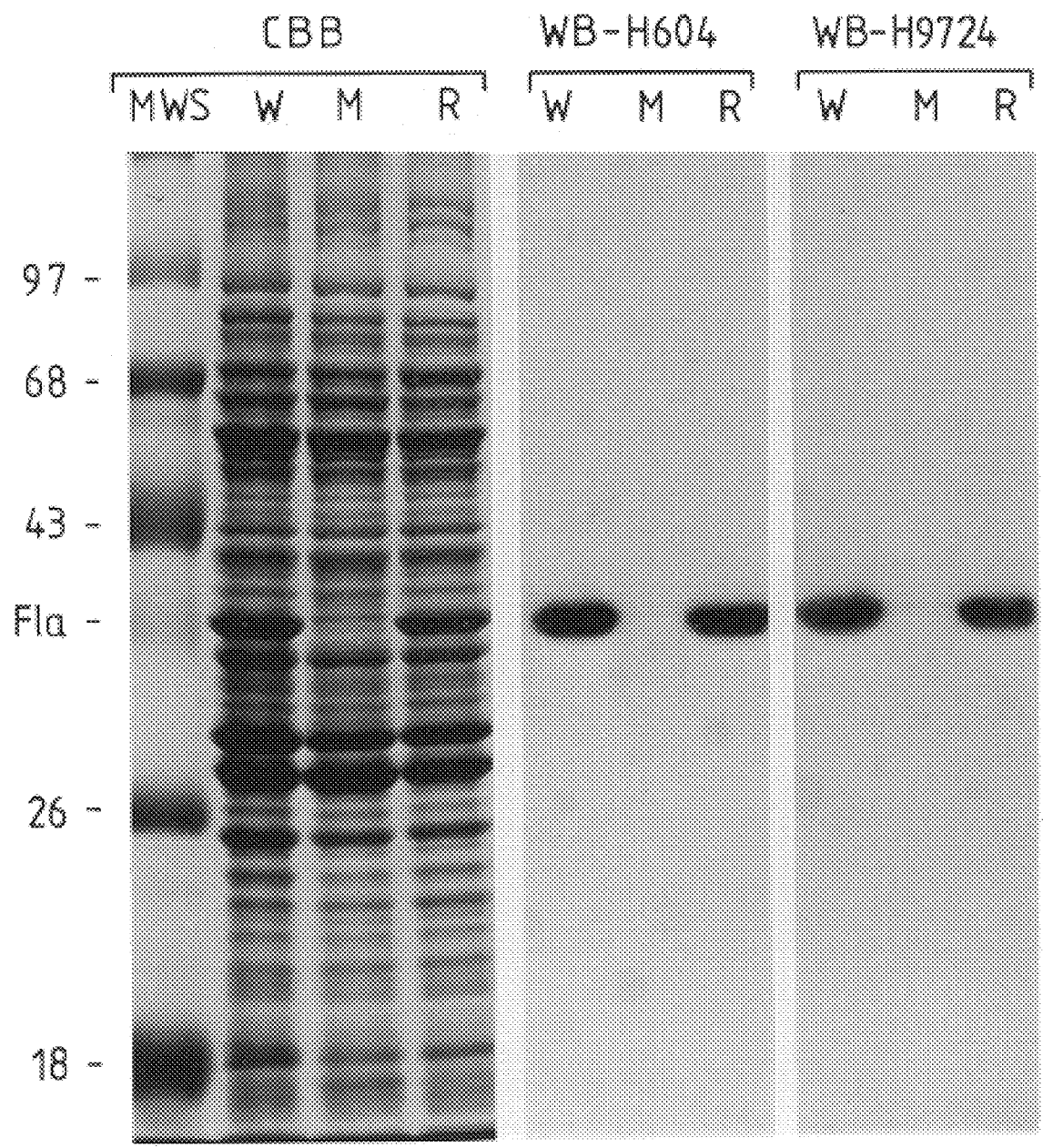
FIG. 3: SDS-PAGE and Western blot (WB) analyses of W, M, and R cells of *Borrelia burgdorferi* strain HB19. Total cell lysates were fractionated on a 15% gel and either stained with Coomasie brilliant blue (CBB) or transferred to nitrocellulose for WB. The blots were incubated with monoclonal antibody H604 or H9724. Bound antibody was detected with radioiodinated protein A. The position of the flagellin (Fla) protein in the gel is indicated. The molecular weight standards (MWS), whose relative molecular weights (×10$^3$) are indicated on the left, were: phosphorylase B (97), bovine serum albumin (68), ovalbumin (43), α-chymotrypsinogen (26), and β-lactoglobulin (18).

The electron microscopy suggested that the flagella-less mutant would have little or no flagellin, the major structural membrane of flagella. This proposition was examined using SDS-PAGE and Western blot analysis (FIG. 3). Those studies were performed as follows.

Whole cell lysates of the different strains were subjected to sodium dodecylsulfate-polyacrylamide gel electrophoresis (SDS-PAGE) as previously described (Bundoc and Barbour 1989). The acrylamide concentration was 12.5%. Western blot analysis was carried out as described previously (Bundoc and Barbour 1989). Hybridoma supernatants were used at a dilution of 1:10, and bound antibody was detected with $^{125}$I-labeled Protein A (New England Nuclear).

SDS-PAGE revealed that the M cells, when compared to W and R cells, lacked a major protein with an apparent molecular weight ($M_r$) of 37 kDa. No other differences between the proteins profiles of W, M, and R were noted by SDS-PAGE.

The identity of the 37 kDa protein with flagellin was confirmed by Western blot analysis with the monoclonal antibodies H9724 and H604. Monoclonal antibody H9724 binds to native and denatured flagellins of different Borrelia spp. (Barbour et al., 1986). Murine monoclonal antibody H605 is directed against the flagellin of *Borrelia burgdorferi* (Barbour et al., 1985).

Even with long exposures, full length or truncated flagellin protein was not detectable. Western blots with polyclonal rabbit antisera to *Borrelia burgdorferi* and Lyme disease patient sera confirmed that M cells appeared to differ from W and R cells only in the absence of a major antigen of approximately 37 kDa (data not shown).

Although the absence of flagellin within the cells of the non-motile mutant was probably the result of failure of expression of the flagellin protein itself, another possible explanation of the findings is that flagellin was produced by the cells but it was not anchored to the hook proteins, and hence lost to the medium. This seemed unlikely, because even transiently associated flagellin should have been detectable in the cells by Western blot. Nevertheless, this alternative explanation was tested by intrinsically labeling the different isolates with $^{35}$S-methionine during growth and then examining the supernatant for evidence of immunoreactive flagellin polypeptides or peptide fragments by immunoprecipitation. The study did not detect the greater presence of flagellin-cross-reactive antigens in medium containing the flagella-less mutant than W and R isolates (data not shown).

Nucleic acid analyses

The preceding studies indicated that the lack of motility and helical morphology of M cells was attributable to absence of cell-associated flagellin protein. To gain the determination of the genetic basis for this mutation we carried out three studies of the nucleic acids of W, M, and R cells as described below. In the first study we examined whether loss of flagella was associated with actual or apparent loss of plasmids in the cell. For this study, a plasmid-enriched fraction of *Borrelia burgdorferi* DNA was prepared and examined by inverted field electrophoresis by methods described by Hinnesbusch, et al., 1990. When the plasmid-rich fraction of DNA from W, M, and R cells was examined by inverted-field gel electrophoresis, no differences in plasmid profiles between the 3 isolates were observed (data not shown).

In the second study of the genetic material we used an oligonucleotide probe for the flagellin gene to assess if there had been deletion of all or a major port of the gene. Total borrelia DNA for Southern blot analysis was extracted by a modification of the method of Meier et al. (Meier, et al., 1985). A washed pellet of approximately $10^9$ borreliae were suspended in 1 ml of 10 mM Tris, pH 8.0–150 mM NaCl-1 mM EDTA (TNE), centrifuged (10,000×g for 3 min), resuspended in 250 $\mu$l of 25% (w/v) sucrose-10 mM Tris, pH 8.0–50 mM EDTA, and placed on ice for 10 min. To this suspension was added 5 $\mu$l of Proteinase K (20 mg/ml of distilled water) and 40 $\mu$l of 10% sodium dodecylsulfate (SDS); cells were lysed by incubation of this mixture at 56° C. for 1 hr. The lysate was extracted with phenol-chloroform and precipitated with ethanol as described (Meier, et al., 1985).

Restriction enzymes were obtained from Boerhinger-Mannheim (Indianapolis, Ind.) and used according to the manufacturer's recommendations. Restriction fragments were transferred to a Nytran membrane with 0.2 $\mu$m pore size (Schleicher and Schuell, In., Keene N.H.). The prehybridization and hybridization solutions were 400 mM NaCl/60 mM sodium citrate/0.1% SDS/0.01% salmon sperm DNA/10×Denhardt's (Bundoc and Barbour 1989). The blots were washed with 15 mM NaCl/1.5 mM sodium citrate/0.1% SDS/1 mM EDTA at 45° C.

An oligonucleotide probe for the *Borrelia burgdorferi* flagellin gene and its mRNA transcript was designed on the basis of the nucleotide sequences of the flagellin genes for the North American strain B31 and the European strain GeHo of *Borrelia burgdorferi* (Gassmann et al., 1989). The 32-mer oligonucleotide was synthesized on an ABI DNA synthesizer as the complement to nucleotides 103–135 of the published sequence of Gassmann et al. 1989. The oligonucleotide was labeled at the 5' end with $\gamma[^{32}P]$-ATP as described (Meier, et al., 1985).

Figure 4A:
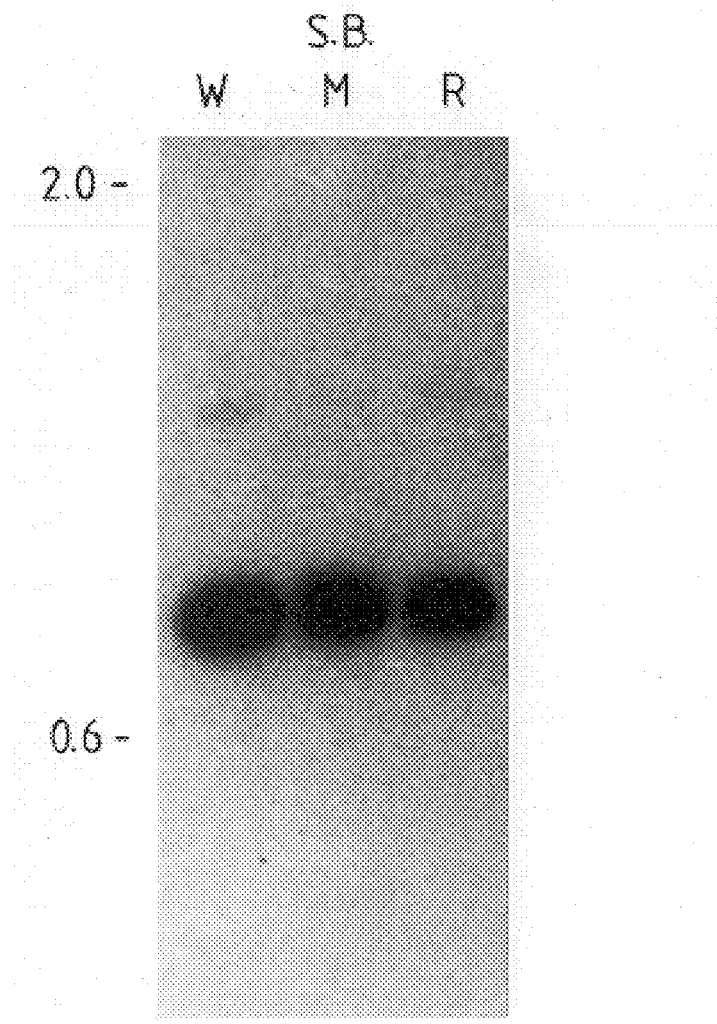
FIG. 4: Southern blot (SB) and Northern blot (NB) analyses of W, M, and R cells of *Borrelia burgdorferi* strain HB19. In the Southern blot Rsa I digests of DNA were separated on a 1.0% agarose gel; the position of the double-stranded size standards (in kilobases) in the gel are indicated are on the left. In the Northern blot total RNA was separated in a 1.5% agarose gel formaldehyde; the positions of the single-stranded size standards (in kilobases) in the gel are shown on the right. For both blots the probe was an oligonucleotide specific for the flagellin gene of *Borrelia burgdorferi* (see text).
Figure 4B:
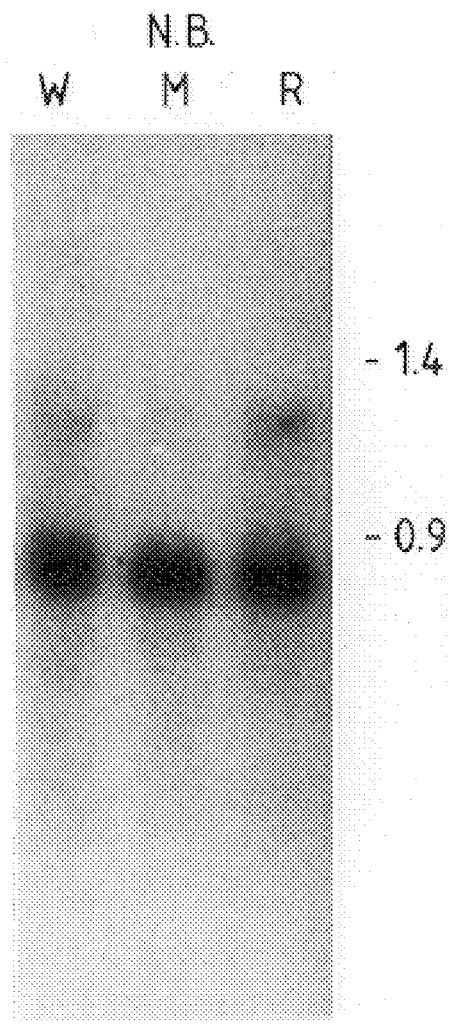
Figure 5A:
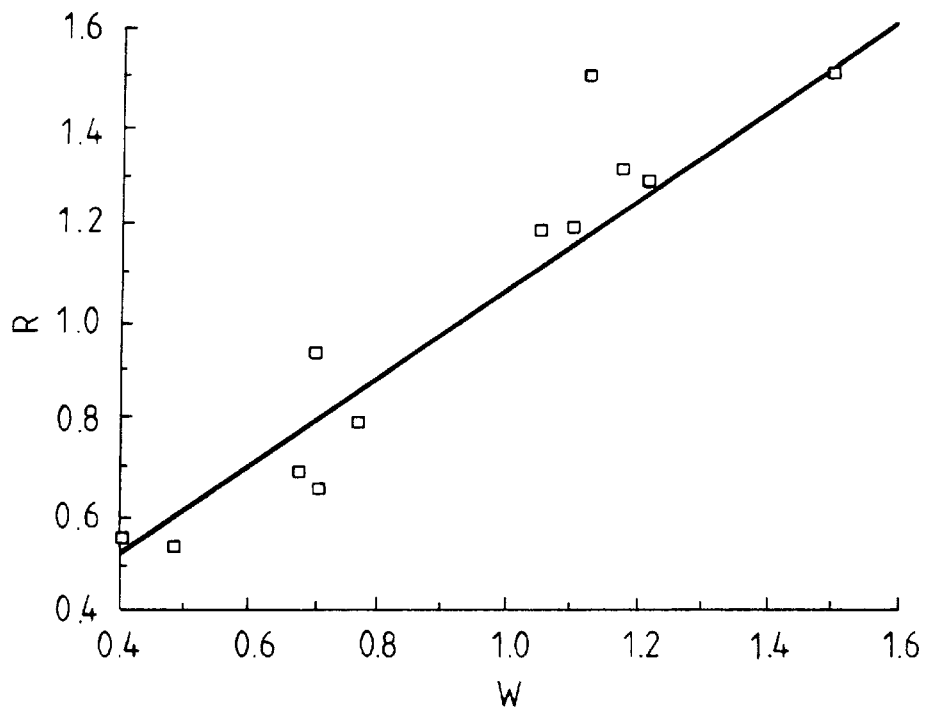
FIG. 5: Comparison of W, M, and R cells of *Borrelia burgdorferi* strain HB19 in an ELISA with Lyme disease patient and control sera. The x and y axes are the absorbance values from the assays. Each point denotes the result of each serum in the pairwise comparison. When absorbance results with sera were ≧1.500 with either of the antigens in the comparison, a single point is shown.
Figure 5B:
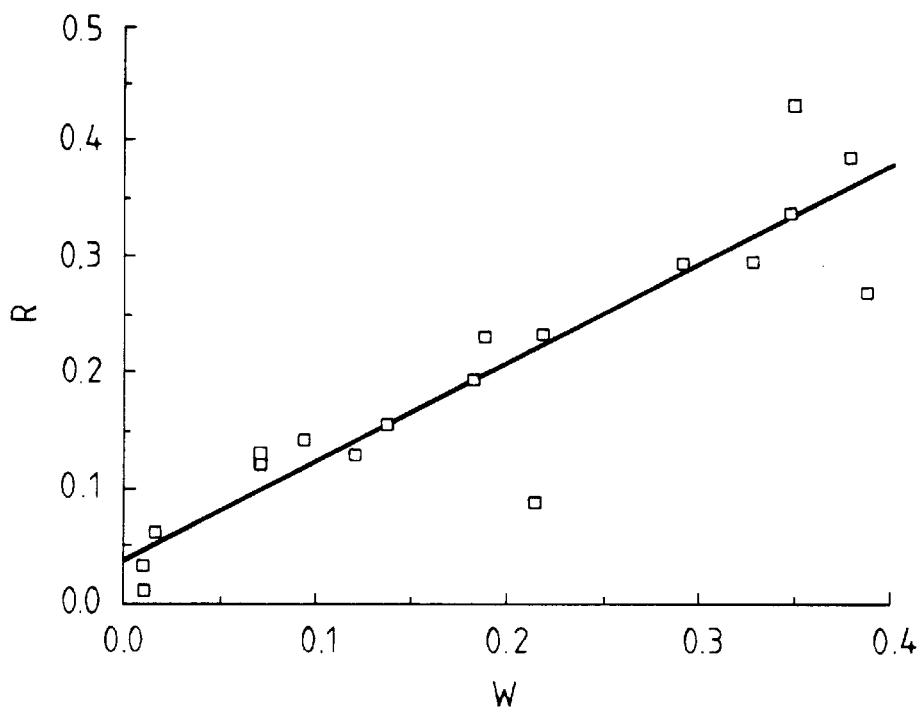
Figure 5C:
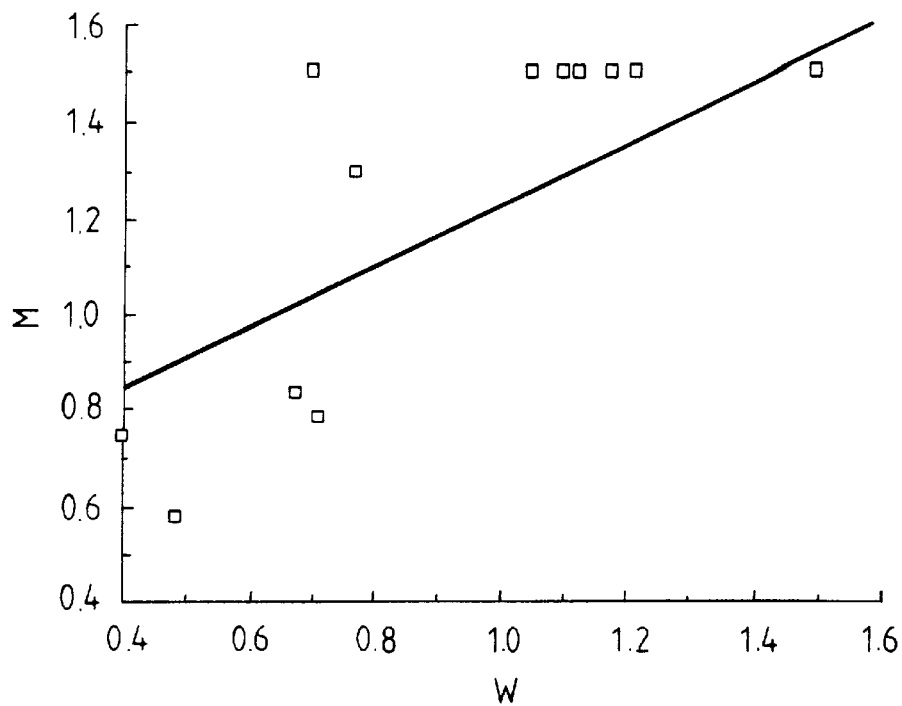
Figure 5D:
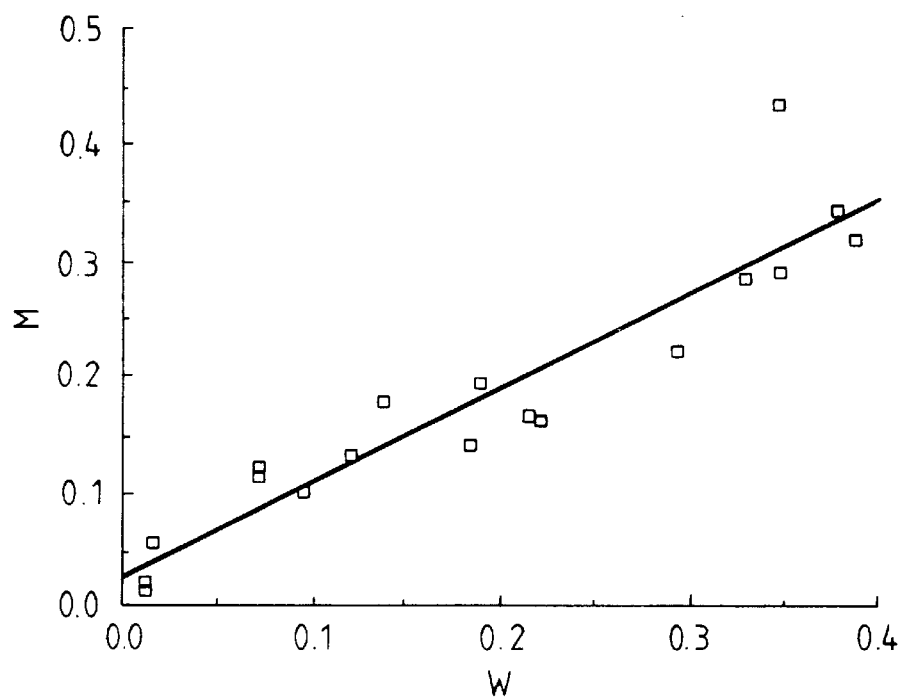
Figure 5E:
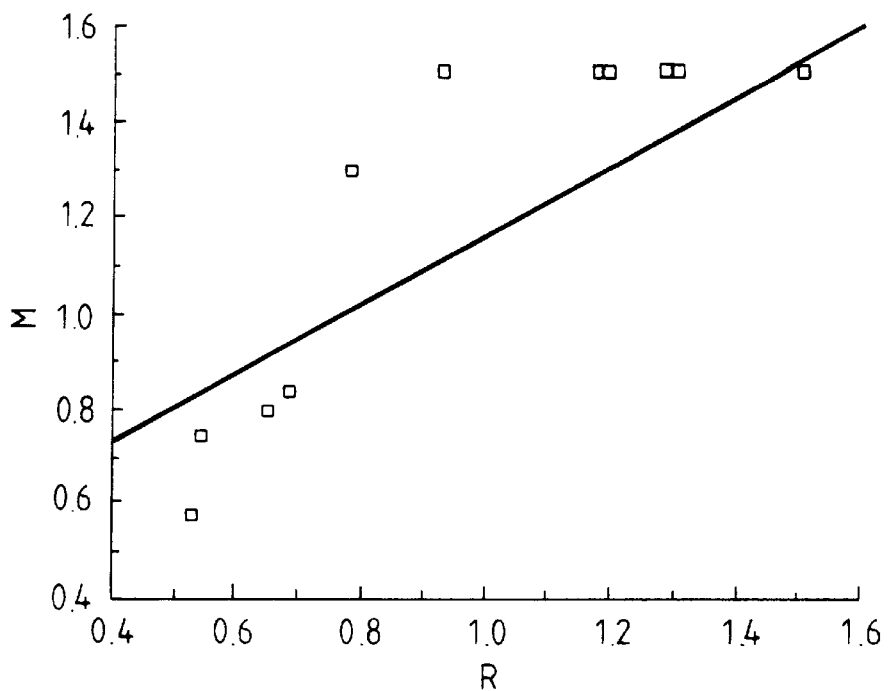
Figure 5F:
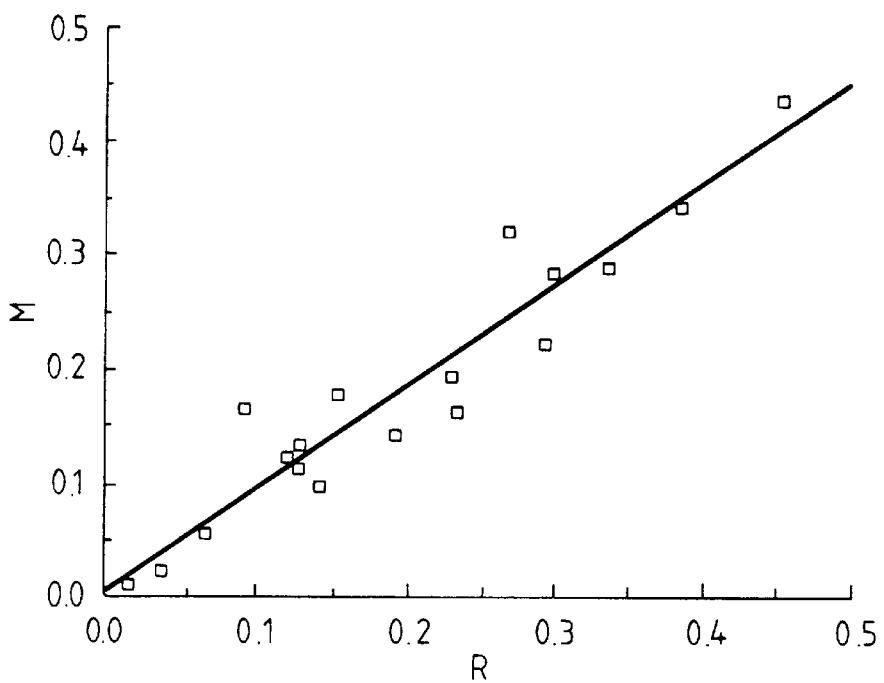

DNA was digested with Rsa I, which would be expected from the published nucleotide sequence of the B31 strain of *Borrelia burgdorferi* to produce a 0.6 kb fragment that contained the complementary sequence to the probe and more than half of the flagellin gene (Gassmann, et al., 1989). The Southern blot analysis is shown in the left panel of FIG. 4. The expected Rsa I fragment was hybridized by the oligonucleotide and there was no difference between the 3 isolates in this respect. The probe did not bind to lambda bacteriophage DNA or *E. coli* DNA under the same conditions (Data not shown). This study indicated that a large deletion in the gene itself had not occurred. The Southern blot analysis also provided genetic evidence that M cells were *Borrelia burgdorferi* and not a contaminant in the culture.

We next sought evidence of transcription of the flagellin gene in M cells. Using the same probe, we examined extracted mRNA of the 3 isolates by Northern blot analysis as described previously (Bundoc and Barbour, 1989). Markers in the formaldehyde denaturing gel were Hae III fragments of bacteriophage M13. The hybridization and washing conditions were those described above for the Southern blot analysis. The results are shown on the right in FIG. 4. The 3 isolates produced a mRNA species that hybridized to the flagellin probe. There was no difference between the size of hybridizing RNA bands of W, M, and R cells.

The absence of evidence of plasmid loss or large deletions in the gene together with evidence that the flagellin gene was fully transcribed suggested that the mutation involved a small number of nucleotides, e.g., a frame shift mutation.

Enzyme-linked immunoabsorbent assay

Antibodies to flagellin have been reported to be a prominent part of the antibody response in early and late Lyme disease (Barbour et al., 1983a; Coleman and Benach 1987; Craft et al., 1986; Grodzicki and Steere, 1988; Wilske, et al., 1988). We compared whole cells of W, M, and R to assess the contribution of antibodies to flagellin in a standard immunologic assay for anti-*Borrelia burgdorferi* antibodies. The aim of the study was to determine whether the total amount of antibody bound would be detectably lower when the flagella-less mutant was used as an antigen than when its flagella-bearing counterparts were used. Sera from patients and controls were examined for their reactivities against whole cells of W, M, and R when equivalent amounts of total cellular protein were used as antigens. Sera from 17 adult patients with Lyme disease of 6 or more weeks duration from Connecticut, Wisconsin, and Lithuania, areas with high incidence of Lyme disease, were used. Sera from 18 healthy adult residents of Rocky Mountain states, a region with a low incidence of Lyme disease, were used as controls.

The enzyme-linked immunoabsorbent assay (ELISA) using whole cells of *Borrelia burgdorferi* was a modification of the method of Magnarelli et al. (Magnarelli and Anderson, 1988). Harvested borreliae were suspended in PBS/Mg and an estimate of total cellular protein in the suspension was made using the Bradford assay (Bio-Rad Laboratories, Richmond, Calif.).

The suspension was diluted 1:1000 in a volume of carbonate buffer (Magnarelli and Anderson, 1988) that gave a protein concentration of 1.4 mg/ml; 50 µl of the diluted cell suspension was added to each well of a flat-bottomed, polystyrene microtiter plate (Corning). After incubation of the plates for 18 hrs at 37° C., 200 ul of 1% (w/v) dried nonfat milk in PBS was added to each dry well. Plates were incubated for 1 hour at 37° C. and washed 4 times with 200 ul of PBS. The plates were incubated for 1 hour at 37° C., and then washed with PBS. Bound IgG antibody was assayed with horseradish peroxidase-conjugated, anti-human IgG (gamma-chain specific) goat antisera (Cal-Biochem, San Diego, Calif.) in 1% nonfat milk/PBS buffer. After incubation for 1 hr. at 37° C., the plates were washed 4 times with 200 ul of PBS. The substrate for the peroxidase reaction was O-phenylenediamine dihydrochloride, and absorbance values at 490 mM were recorded on a Dynatech ELISA reader (Model #580). The maximum absorbance value read was 1.5000.

The mean absorbance values (±standard error) for the 17 patient sera were 1.09 (±0.09) for W, 1.31 (±0.08) for M, and 1.15 (±0.09) for R cells. Analogous determinations for 18 control sera were 0.19 (±0.03), 0.18 (±0.03), and 0.20 (±0.03), respectively. FIG. 5 shows the pairwise comparisons for W, M, and R cells when patient and control sera were used in the ELISA. There was good correlation between W and R cells for patient sera. Furthermore, when control sera were used the 3 isolates gave comparable results. Surprisingly, the flagella-less M cells had an equal or higher absorbance reading for each patient serum when compared with W and R cells. Many of the values with M cells in the ELISA were ≧1.50, the absorbance reading maximum. When sera were diluted 1:1000 instead of 1:500 consistently higher absorbance values with M cells as compared with W and R cells was observed (data not shown).

This study showed that the flagella-less cells were equal if not superior to flagella-bearing spirochetes in an immunologic assay that measures total IgG against *Borrelia burgdorferi*.

Endothelial cell adhesion and penetration assay

Assays for adhesion and penetration of intrinsically-labeled spirochetes to and through human umbilical vein endothelial (HUVE) cells were carried out as described by Comstock and Thomas (Comstock and Thomas, 1989). HUVE cells were isolated from freshly delivered human umbilical cords by the method of Jaffe et al. (Jaffe, et al., 1972). All assays were done in triplicate.

For assessing adherence to HUVE cells, borreliae were intrinsically radiolabeled with [35S]-methionine, washed with PBS, and resuspended to a density of $10^8$ bacteria and specific activity of $2.4 \times 10^5$ cpm per ml of Medium 199 with 15% fetal calf serum (FCS). To confluent HUVE cell monolayers grown in 24-well plates were added 0.5 ml aliquots. Following a 3 hr. incubation at 37° C., monolayers with associated organisms were washed, solubilized, mixed with scintillation cocktail, and counted by scintillation (Thomas and Comstock, 1989).

For penetration experiments, $2.5 \times 10^4$ HUVE cells were seeded onto sterile polycarbonate membrane culture plate inserts (3µ pore size; 6.5 mm dia; Nucleopore, Pleasonton, Calif.). Chambers were placed in 24 well plates containing 1 ml Medium 199–15% FCS per well and incubated for 48 hrs, at which time the monolayers were confluent and possessed high transendothelial electrical resistance. Bacteria were quantitated by darkfield microscopy, centrifuged for 15 min at 17,000×g, and resuspended in M199-FCS. For each assay, 0.2 ml samples containing $3 \times 10^8$ bacteria were added to the upper portions of the chambers (above the monolayers). Following a 4 hr incubation at 37° C. in 5% $CO_2$ in air, aliquots from beneath the filters were removed and spirochetes were counted by darkfield microscopy (Comstock and Thomas, 1989). In this study $3 \times 10^8$ spirochetes with a specific activity of $5 \times 10^5$ cpm were added to each chamber in a volume of 0.2 ml, and the samples were incubated at 37° C. for 4 hrs. At the end of the incubation the amount of radioactivity in the lower chamber was measured.

The adhesion of intrinsically labeled borreliae to human endothelial cells was studied. The binding of the isolates W, M, and R were compared with each other and also with an early passage isolate of the parent strain HB19. The results of this study showed that approximately 20% fewer of the flagella-less M spirochetes than the W and R spirochetes bound to the cells. As had been demonstrated previously (Thomas and Comstock 1989), the high passage isolates bound to cells less well than the early passage version of the HB19 strain.

TABLE 1

Host Cell Association Assay

| Isolate | Average cpm (SD) Cell associated | Average % of inoculum Cell Associated |
|---|---|---|
| W | 6880 (342) | 5.7 (0.3) |
| M | 5173 (276) | 4.3 (0.2) |
| R | 6256 (336) | 5.2 (0.3) |
| Low passage HB19 | 8208 (425) | 6.8 (0.4) |

In the next experiment we studied the penetration of the same four isolates through human umbilical vein endothelial monolayers. In this study $3 \times 10^8$ bacteria with a specific activity of $5 \times 10^5$ cpm were added to each chamber, and the samples were incubated at 37° C. for 4 hours. At the end of the incubation the amount of radioactivity in the lower chamber was measured. The results are given in Table 2.

Neither the W nor R isolates of HB19 penetrated HUVE cells as well as the low-passage isolate of HB19. R cells, which penetrated the monolayer less well than W, had undergone two more clonings by colony plating or limiting dilation than W cells. The greatest difference between the 4 isolates, however, was between M cells and the motile forms of HB19. Approximately 95% fewer M cells than W or R penetrated the cell monolayer. This decrease was greater than could be attributed to decreased adherence.

The penetration of HUVE cells by the W, M, and R spirochetes was also examined using transmission electron microscopy. For this procedure, membrane filters with attached monolayers were prepared as described previously (Comstock and Thomas, 1989). The membrane filters were cut from the culture plate inserts, rinsed in PBS, fixed in glutaraldehyde, stained, dehydrated and embedded in epoxy resin. Transverse thin sections were placed on copper mesh grids and stained with lead citrate and uranyl acetate prior to examination in a Philips TEM 400 microscope. FIG. 6 shows a typical result when M and R organisms were incubated with HUVE cell monolayers. In cross-section, both R and M cells had discernible protoplasmic cylinders and outer sheaths but M cells, unlike R cells, did not have axial flagella (Insets in FIGS. 6A and 6B). Both R and M spirochetes adhered to the HUVE cell surface in a manner superficially indistinguishable from that observed with an early passage isolate of strain HB19 (Comstock and Thomas, 1989). When the cytoplasm of HUVE cells was examined in thin sections, however, differences between R and M in the number of intracellular spirochetes were noted. Whereas R spirochetes were observed in 57 (95%) of 60 HUVE cells examined, only 2 (3%) of 65 HUVE cells showed evidence of containing an intracellular M cell ($p<0.0001$; Fisher's exact test).

TABLE 2

Penetration of Cell Monolayers

| Isolate | Average cpm (SD) in lower chamber | Average % of inoculum in lower chamber (SD) |
|---|---|---|
| W | 33,504 (1144) | 6.8 (0.2) |
| M | 887 (283) | 0.2 (0.1) |
| R | 12,810 (569) | 2.6 (0.1) |
| Low passage HB19 | 41,387 (1709) | 8.4 (0.4) |

From these studies we concluded that flagella less strains could be isolated from *Borrelia burgdorferi* cultures and maintained in culture. Furthermore, the absence of flagella does not reduce the efficacy of a *Borrelia burgdorferi* for serologic testing for antibodies to *Borrelia burgdorferi* in patients with Lyme borreliosis. Indeed, the use of a flagella-less microorganisms in a serologic assay is likely to improve the sensitivity and specificity of the assay. Although applicants are not bound by theory, the possible reasons for this are the following: (a) When flagella are not present, the relative amounts of other proteins in the suspension on a protein concentration basis increases. One or more of these other proteins (or non-proteins) may be more important than flagella for diagnostic purposes. (b) Flagella are likely a major source of false-positive reactions, because of the cross-reactivities between the flagella of *Borrelia burgdorferi* and those of other bacteria. When flagella are not present, the specificity of the assay may improve. The flagella-less isolate could be used in place of borrelia with the wild-type phenotype in immunofluorescence, ELISA-base, and Western blot assays.

EXAMPLE III

Immunization of rats with *Borrelia burgdorferi*

A flagella-less microorganism may be safer to use as the basis of a whole-cell or subunit vaccine for protection against Lyme disease or other Borrelia infections than an antigen preparation containing flagella. Studies have demonstrated cross-reactions between flagellar-associated antigens and human tissues, including nerve and muscle. It is possible that vaccines containing large or small amounts of flagellar materials will induce an autoimmune reaction in the recipient.

A flagella-less borreliae would also be safer than a wild-type strain for vaccines because there is less danger of tissue invasion by the flagella-less strain. Finally, immunization with the flagella-less microorganism provides the additional advantage of allowing one to more accurately assess vaccine efficacy.

The following study demonstrates preparation of an immunogenic composition of the flagella-less *Borrelia burgdorferi* to induce an immune response in animals.

Adult Fisher rats were immunized with 100 µg of total cellular protein as whole spirochetes in complete Freund's adjuvant on day 0 and were bled on day 14. Two rats were immunized with W cells, and 2 rats were immunized with M cells. Two weeks later sera were examined for antibodies to a low-passage isolate of *B. burgdorferi* and to the relapsing fever agent *Borrelia hermsii* by Western blot analysis to establish that the flagella-less mutant would elicit antibodies to non-flagellin borrelial components. Unimmunized rats were used as a control in the Western blot analysis. The locations in the blots of OspA and OspB proteins for *B. burgdorferi* and the flagellin proteins of both *B. burgdorferi* and *B. hermsii* were identified with monoclonal antibodies.

FIG. 7 shows the results of this experiment. All rat sera, including the control sera, bound to a *B. hermsii* protein with an apparent size of approximately 50 kDa. In addition, rats immunized with W and M cells all had antibodies against the OspA and OspB proteins as well as a lower-molecular weight protein of approximately 22 kDa. Rats immunized with W cells had antibodies to the 37 kDa flagellin of *B. burgdorferi*, and, by reason of antigenic similarity (Barbour, et al., 1986), also to the 36 kDa flagellin of *B. hermsii*. In contrast, rats immunized with M cells did not have any detectable antibodies to flagellin of either species.

Rats immunized with M cells also differed with rats immunized with W cells in another respect. Whereas the latter rats had antibodies to a protein of approximately 35 kDa, the former rats did not. The 35 kDa protein may be a truncated flagellin protein or the result of hydrolysis or proteolysis in either the cells or after lysis.

In additional studies, rats were immunized intramuscularly with 20 μg total protein of borreliae in complete Freund's adjuvant. After 6 weeks, the rats were bled and their serum was analyzed by ELISA, essentially as described above. The results of this experiment shown in Table 3, indicated that immunization with M cells induced a significant immune response against W cells.

TABLE 3

ELISA Test With Serum Diluted 1:1,000

| Rat # | Immunogen | ELISA antigen | Absorbance Value |
|---|---|---|---|
| 1 | W cells | W cells | 0.713 |
|   |         | M cells | 0.727 |
| 2 | W cells | W cells | 0.592 |
|   |         | M cells | 0.629 |
| 3 | M cells | W cells | 0.555 |
|   |         | M cells | 0.449 |
| 4 | M cells | W cells | 0.589 |
|   |         | M cells | 1.082 |
| 5 | Adjuvant alone | W cells | 0.010 |
|   |         | M cells | 0.014 |
| 6 | Adjuvant alone | W cells | 0.015 |
|   |         | M cells | 0.013 |

In yet other studies, the antibodies of the immunized rats were analyzed for the ability to neutralize borreliae. For these studies the highest dilution of unheated, fresh serum from rats immunized as described above which inhibited the growth of W in BSK II medium was determined in duplicate and is shown in Table 4 below. The initial concentration of borreliae in the medium was $10^7$ cells per milliliter of medium. The borreliae were grown in microtiter plates containing 200 microliters per well. The cultures were grown at 34° C. for 3 days and then examined for growth by visual assessment of color change of the phenol red indicator in medium and by phase microscopy for evidence of motility.

TABLE 4

| IMMUNOGEN | | |
|---|---|---|
| W cells | M cells | Adjuvant alone |
| 1:3,000 | 1:3,000 | ≦1:10 |

As shown, serum from immunized rats, even at a dilution of 1:3,000 was capable of neutralizing B. burgdorferi. Thus, when used to immunize rats, flagella-less (M) cells were as effective as flagella-bearing (W) cells in eliciting antibodies to B. burgdorferi as determined by ELISA and by growth inhibition assay.

This experiment demonstrated that flagella-less borreliae can be used to immunize animals and that the immunized animals produce antibodies to the major outer membrane proteins of B. burgdorferi: OspA, OspB, and the lower molecular weight protein of about 22K as effectively as animals immunized with wild-type cells. The experiment also showed that when animals are immunized with the flagella-less mutant they do not make antibodies against flagellin proteins and that antibodies from animals immunized with the flagella-less borreliae are capable of neutralizing wild type borreliae.

The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

For example, numerous methods for immunoassay may be used. In addition, variations in vaccine preparation may be employed. It is apparent that the invention may also be utilized, with suitable modifications within the state of the art. It is the Applicants intention in the following claims to cover all such equivalent modifications and variations which fall within the true spirit, and scope of the invention.

REFERENCES

The following references may facilitate understanding or practice of certain aspects of the present invention, and are incorporated by reference herein. Inclusion of a reference in this list is not intended to and does not constitute an admission that such reference represents prior art with respect to the present invention, however.

REFERENCES

1. E. Aberer et al., Molecular mimicry and Lyme borreliosis: a shared antigenic determinant between *Borrelia burgdorferi* and human tissue, *Ann. Neurol* 1989; 26:732–7.
2. A. G. Barbour, Isolation and cultivation of Lyme disease spirochetes, Yale *J. Biol. Med.* 1984; 57:521–5.
3. A. G. Barbour et al., Antibodies of patients with Lyme disease to components of the Ixodes dammini spirochete, *J. Clin. Invest*. (1983a); 72:504–15.
4. A. G. Barbour et al., Isolation of a cultivable spirochete from Isodes ricinus ticks of Switzerland, *Curr. Microbiol.* 1983b; 8:123–126.
5. A. G. Barbour et al., A Borrelia-specific monoclonal antibody binds to a flagellar epitope, *Infect. Immun.* 1986; 52:549–54.
6. A. G. Barbour et al., Heterogeneity of major proteins in Lyme disease borreliae: a molecular analysis of North American and European isolates, *J. Infect. Dis.* 1985; 152:478–84.
7. A. G. Barbour et al., Variation in a major surface protein of Lyme disease spirochetes, *Infect. Immun.* 1984; 45:94–100.
8. A. G. Barbour et al., Variable major proteins of *Borrelia hermsii, J. Exp. Med.* 1982; 156:1312–24.
9. A. G. Barbour and S. F. Hayes; Biology of Borrelia species; *Microbial Rev.* 1986; 50:381–400.
10. A. G. Barbour, Laboratory aspects of Lyme borreliosis; *Clin. Microbiol. Rev.* 1988; 1:399–414.
11. J. L. Benach et al., spirochetes isolated from the blood of two patients with Lyme disease, *N. Engl. J. Med.* 1983; 308:740–2.
12. B. W. Berger et al., Lyme disease is a spirochetosis: a review of the disease and evidence for its cause, *Am. J. Dermatolpathol.* 1983; 5:111–24.
13. D. B. Bromley and N. W. Charon, Axial filament involvement in the motility of *Leptospira interrogans, J. Bacteriol.* 1979; 137:1406–1412.
14. V. G. Bundoc and A. G. Barbour, Clonal polymorphisms of outer membrane protein OspB of *Borrelia burgdorferi, Infect. Immun.* 1989; 57:2733–41.
15. M. B. Caldwell et al., Reversible expression of flagella in Campylobaccter jejuni, *Infect. Immun.* (1985); 50:941–943.
16. M. Carsiotis et al., A Salmonella typhimurium virulence gene linked to flg., *Infect. Immun.* 1989; 57:3276–3280.
17. C. A. Ciesielski et al., "The geographic distribution of Lyme disease in the United States; In: Benach and Bosler (eds.), Lyme Disease and Related Disorders, vol. 539, New York, The New York Academy of Sciences. 1988:283–8.

18. J. L. Coleman and J. L. Benach, Isolation of antigenic components from the Lyme disease spirochete: their role in early diagnosis, *J. Inf. Dis.* 1987; 155:756–765.

19. L. E. Comstock and D. D. Thomas, Penetration of endothelial cell monolayers by *Borrelia burgdorferi*, *Infect. Immun.* 1989; 57:1626–8.

20. J. E. Craft et al., Antigens of *Borrelia burgdorferi* recognized during Lyme disease. Appearance of a new immunoglobulin M. response and expansion of the immunoglobulin G late in the illness, *J. Clin. Invest.* 1986; 78:934–939.

21. R. J. Dattwyler et al., Seronegative Lyme disease, dissociation of specific T-B-lymphocyte responses to *Borrelia burgdorferi*, *N. Engl. J. Med.* 1988; 139:1441–6.

22. E. J. Dekonenko et al., Lyme Borreliosis in the Soviet Union: a cooperative US-USSR report; *J. Infect. Dis.* 1988; 158:748–53.

23. J. Duffy et al., Diagnosing Lyme disease: the contribution of serologic testing; *Mayo Clin. Proc.* 1988; 63:1116–21.

24. P. H. Duray, The surgical pathology of human Lyme disease: an enlarging picture; *Am. J. Surg. Pathol.* 1987; 11:47–60.

25. G. S. Gassman et al., Nucleotide sequence of a gene encoding the *Borrelia burgdorferi* flagellin, *Nucl. Acids Res.* 1989; 17:3590.

26. S. F. Goldstein and N. W. Charon, Motility of the spirochete Leptospira, *Cell Motil. Cytoskel.* 1988; 9:101–110.

27. R. L. Grodzicki et al., Comparison of immunoblotting and indirect enzyme-linked immunosorbent assay using different antigen preparations for diagnosing early Lyme disease, *J. Infect. Dis.* 1988; 157:790–7.

28. K. Hansen and E. Asbrink, Serodiagnosis of erythema migrans and acrodermatitis chronica atrophicans by the *Borrelia burgdorferi* flagellum enzyme-linked immunosorbent assay, *J. Clin. Microbiol.* 1989; 27:545–554.

29. K. Hansen et al., Immunochemical characterization of and isolation of the gene for a *Borrelia burgdorferi* immunodominant 60-kilodalton antigen common to a wide range of bacteria, *Infect. Immun.* 1988a; 56:2047–53.

30. K. Hansen et al., Measurement of antibodies to the *Borrelia burgdorferi* flagellum improves serodiagnosis in Lyme disease, *J. Clin. Microbiol* 1988; 26:338–46.

31. C. W. Hedberg et al., An interlaboratory study of antibody to *Borrelia burgdorferi*, *J. Infect. Dis.* 1987; 155:1325–7.

32. J. Hinnebusch et al., Cloning and sequence analysis of linear plasmid telomeres of the bacterium *Borrelia burgdorferi*, *Mol. Microbiol.* 1990; 4:811–820.

33. S. C. Holt, Anatomy and chemistry of spirochetes, 1978; 38:114–160.

34. M. Homma et al., Hook-associated proteins essential for flagellar filament formation in Salmonella typhimurium, *J. Bacteriol.* 1984; 157:100–8.

35. E. Jaffe et al., Culture of human endothelial cells derived from human umbilical cord veins, Circulation 1972; 46:211–223.

36. Johnson, et al., Active Immunization of Hamsters against Experimental Infection With *Borrelia Burgdorferi*, *Infect. Immun.*, 54:897–898 (1986).

37. G. W. Jones and R. Freter, Adhesive properties of Vibrio cholerae: nature of the interaction with isolated rabbit brush border membranes and human erythrocytes, *Infect. Immun.* 1976; 14:240–245.

38. R. J. Limberger and N. W. Charon, Treponema phagedenis has at least two proteins residing together on its periplasmic flagella, *J. Bacteriol.* 1986; 166:105–112.

39. H. A. Lockman and R. Curtiss III, *Salmonella typhimurium* mutants lacking flagella or motility remain virulent in BALB/c mice, *Infect. Immun.* 1990; 58:137–143.

40. L. A. Magnarelli and J. F. Anderson, Enzyme-linked immunosorbent assays for the detection of class-specific immunoglobulins to *Borrelia burgdorferi*, *Am. J. Epidemiol.* 1988; 127:818–825.

41. L. A. Magnarelli et al., Enzyme-linked immunosorbent assays for Lyme disease: reactivity of subunits of *Borrelia burgdorferi*, *J. Infect. Dis.* 1989; 159:43–9.

42. L. A. Magnarelli, Serologic diagnosis of Lyme disease, In: Benach and Bosler (eds.); Lyme Disease and Related Disorders, vol. 539, New York, The New York Academy of Sciences, 1988:154–61.

43. J. T. Meier et al., Antigenic variation is associated with DNA rearrangements in a relapsing fever Borrelia, *Cell* 1985; 41:403–9.

44. J. H. Miller, Pathways of mutagenesis revealed by analysis of mutational specificity; In Genetics of Bacteria, J. Scaife, D. Leach and A. Galizzi ed. (London: Academic Press), 1985; pp. 25–40.

45. T. C. Montie et al., Loss of virulence associated with absence of flagellum in an isogenic mutant of *Pseudomonas aeruginosa* in the burned-mouse model, *Infect. Immun.* 1982; 38:1296–8.

46. H. K. Park et al., Erythema chronicum migrans of Lyme disease: diagnosis by monoclonal antibodies; *J. Am. Acad. Dermatol.* 1986; 15:406–10.

47. N. S. Pedersen et al., Serodiagnosis of syphilis by an enzyme-linked immunosorbent assay for IgG antibodies against the Reiter treponeme flagellum, *Scand. J. Immunol.* 1982; 15:341–348.

48. F. Sadallah et al., Production of specific monoclonal antibodies to *Salmonella typhi* flagellin and possible application to immunodiagnosis of typhoid fever, *J. Inf. Dis.* 1990; 161:59–64.

49. L. H. Sigal and A. H. Tatum, IgM in the Sera of Patients with lyme Neurologic Disease Bind to Cross-reacting Neuronal and *Borrelia burgdorferi* Antigens, *Ann. NY Acad. Sci.* 539:422–424 (1988).

50. G. Stanek et al., "European Lyme Borreliosis, In: Benach and Bosler (eds.), Lyme Disease and Related Disorders, vol. 539, New York, The New York Academy of Sciences. 1988:274–82.

51. A. C. Steere et al., Erythema chronicum migrans and Lyme arthritis: the enlarging clinical spectrum, *Ann. Intern. Med.* 1977; 86:685–98.

52. A. C. Steere et al., Successful parenteral penicillin therapy of established Lyme arthritis, *N. Engl. J. Med.* 1985; 312:869–74.

53. A. C. Steere et al., Neurologic abnormalities of Lyme disease: successful treatment with high-dose intravenous penicillin, *Ann. Intern. Med.* 1983; 99:767–72.

54. A. C. Steere et al., The spirochetal etiology of Lyme disease, *N. Engl. J. Med.* 1983; 308:733–40.

55. A. C. Steere, Lyme disease, New Engl. J. Med. 1989; 321:586–596.

56. A. C. Steere et al., Association of chronic Lyme arthritis with HLA-DR4 and HLA-DR2 alleles, *New Engl. J. Med.* 1990; 323:219–223.
57. D. D. Thomas and L. E. Comstock, Interaction of Lyme disease spirochetes with cultured eucaryotic cells, *Infect. Immun.* 1989; 57:1324–6.
58. R. Wallich et al., The *Borrelia burgdorferi* flagellum-associated antigen (flagellin): molecular cloning, expression, and amplification of the gene, *Infect. Immun.* 1990; 58:1711–1719.
59. B. Wilske et al., Immunochemical analysis of the immune response in late manifestations of *Lyme borreliosis, Zentralbl Bakteriol Mikrobiol Hyg* [*a*] 1988; 267:549–58.
60. C. R. Woese, Bacterial evolution, *Microbiol. Rev.* 1987; 51:221–271.

---

We claim:

1. An immunogenic composition for inducing an immune response to *Borrelia burgdorferi* comprising whole cells from a substantially purified culture of flagella-less *Borrelia burgdorferi* having all the phenotypic characteristics of ATCC No. 55131 and a pharmaceutically acceptable carrier.

2. A method for inducing an immune response of a mammal to *Borrelia burgdorferi* comprising administering an immunogenic dose of the immunogenic composition of claim 1 to said mammal.

3. An immunogenic composition for inducing an immune response to *Borrelia burgdorferi* comprising whole cells of a flagella-less Borrelia of ATCC No. 55131 and a pharmaceutically acceptable carrier.

4. The composition of claim 1 comprising live flagella-less Borrelia microorganisms.

5. The composition of claim 1 comprising killed flagella-less Borrelia microorganisms.

* * * * *